United States Patent
Moriya et al.

(10) Patent No.: US 12,426,796 B2
(45) Date of Patent: Sep. 30, 2025

(54) BRAIN MEASUREMENT APPARATUS

(71) Applicants: HAMAMATSU PHOTONICS K.K., Hamamatsu (JP); Kyoto University, Kyoto (JP)

(72) Inventors: Takahiro Moriya, Hamamatsu (JP); Takenori Oida, Hamamatsu (JP); Akinori Saito, Hamamatsu (JP); Motohiro Suyama, Hamamatsu (JP); Tetsuo Kobayashi, Kyoto (JP)

(73) Assignees: HAMAMATSU PHOTONICS K.K., Hamamatsu (JP); Kyoto University, Kyoto (JP)

( * ) Notice: Subject to any disclaimer, the term of this patent is extended or adjusted under 35 U.S.C. 154(b) by 479 days.

(21) Appl. No.: 17/829,442

(22) Filed: Jun. 1, 2022

(65) Prior Publication Data
US 2022/0386888 A1  Dec. 8, 2022

(30) Foreign Application Priority Data
Jun. 4, 2021  (JP) ................ 2021-094314

(51) Int. Cl.
*A61B 5/055* (2006.01)

(52) U.S. Cl.
CPC ................ *A61B 5/055* (2013.01)

(58) Field of Classification Search
None
See application file for complete search history.

(56) References Cited

U.S. PATENT DOCUMENTS

| | | | | |
|---|---|---|---|---|
| 5,315,276 | A * | 5/1994 | Huson | G01R 33/383 324/319 |
| 5,592,090 | A * | 1/1997 | Pissanetzky | G01R 33/3806 324/369 |
| 5,942,898 | A * | 8/1999 | Petropoulos | G01R 33/385 324/318 |
| 8,305,078 | B2 | 11/2012 | Savukov et al. | |

(Continued)

FOREIGN PATENT DOCUMENTS

| | | |
|---|---|---|
| CN | 104146710 A | 11/2014 |
| JP | H4-132537 A | 5/1992 |

(Continued)

OTHER PUBLICATIONS

Boto, Elena et al., "Moving magnetoencephalography towards real-world applications with a wearable system," Nature, Mar. 29, 2018, vol. 555, pp. 657-661.

(Continued)

*Primary Examiner* — Rodney E Fuller
(74) *Attorney, Agent, or Firm* — Faegre Drinker Biddle & Reath LLP

(57) ABSTRACT

A brain measurement apparatus includes: a static magnetic field forming unit for forming a static magnetic field in a measurement area; a gradient magnetic field coil for forming a gradient magnetic field in the measurement area; a transmission coil for transmitting a transmission pulse toward a subject in the measurement area; a detection coil for detecting a nuclear magnetic resonance signal generated in the subject by transmission of the transmission pulse; and a generator for generating an MR image based on the nuclear magnetic resonance signal detected by the detection coil.

8 Claims, 14 Drawing Sheets

(56) References Cited

U.S. PATENT DOCUMENTS

| | | |
|---|---|---|
| 8,519,705 B2 | 8/2013 | Savukov et al. |
| 2011/0025332 A1 | 2/2011 | Abele et al. |
| 2016/0069968 A1 | 3/2016 | Rothberg et al. |
| 2020/0040429 A1 | 2/2020 | Luma |
| 2021/0325493 A1* | 10/2021 | Kirsch ............... G01R 33/3806 |
| 2021/0386347 A1 | 12/2021 | Moriya et al. |

FOREIGN PATENT DOCUMENTS

| | | | |
|---|---|---|---|
| JP | 3112474 B2 * | 11/2000 | ........... G01R 33/381 |
| JP | 2006-191957 A | 7/2006 | |
| JP | 2012-239723 A | 12/2012 | |
| JP | 2020-146408 A | 9/2020 | |
| JP | 2020-151023 A | 9/2020 | |
| WO | 2012/120732 A1 | 9/2012 | |
| WO | WO-2012/131635 A1 | 10/2012 | |

OTHER PUBLICATIONS

Iivanainen, Joonas et al., "On-scalp MEG system utilizing an actively shielded array of optically-pumped magnetometers," NeuroImage, 2019, 194, pp. 244-258.

Körber, Rainer et al., "SQUIDs in biomagnetism: a roadmap towards improved healthcare," Superconductor Science and Technology, 2016, 29, pp. 1-30.

Sarracanie, Mathieu et al., "Low-Cost High-Performance MRI," Scienticfic Reports, Oct. 15, 2015, pp. 1-9.

Tsai, L. L. et al., "An Open-Access, Very-Low-Field MRI System for Posture-Dependent $^3$He Human Lung Imaging," J Magn Reson., Aug. 2008, 193(2), pp. 1-29.

Hiroki Yoshikawa, "High Magnetic Field Strength in MRI Systems," Journal of the Japanese Society of Magnetic Resonance in Medicine, Oct. 15, 2006, vol. 26, No. 4, pp. 162-164.

Carl A. Michal, "Low-cose low-field NMR and MRI: Instrumentation and applications," Journal of Magnetic Resonance, Oct. 31, 2020, vol. 319, p. 106800 (1-11).

* cited by examiner

BRAIN MEASUREMENT APPARATUS

TECHNICAL FIELD

The present disclosure relates to a brain measurement apparatus.

BACKGROUND

Patent Literature 1 (Japanese Unexamined Patent Publication No. 2012-239723) describes a magnetic resonance imaging apparatus. A cylindrical static magnetic field magnet for forming a static magnetic field in an imaging region for a gantry in which the imaging region is formed, a cylindrical gradient magnetic field coil for forming a gradient magnetic field in the imaging region, and a WB coil for transmitting the RF magnetic field pulse to the entire imaging region are coaxially built in the apparatus.

Incidentally, in Non-Patent Literature 1 (Sarracanie et al., Low-Cost High-Performance MRI, SCIENTIFIC REPORTS, 15 Oct. 2015, p. 1-9), it has been pointed out that when the static magnetic field magnet is strong and huge, very strict infrastructure requirements are made. On the other hand, Non-Patent Literature 1 proposes to use a simple coiled electromagnet of about 6.5 mT. In this case, however, when the static magnetic field is formed, the power consumption increases to, for example, 6 kW to 7 kW.

SUMMARY

It is an object of the present disclosure to provide a brain measurement apparatus capable of reducing power consumption.

A brain measurement apparatus according to the present disclosure includes: a static magnetic field forming unit configured to form a static magnetic field in a measurement area; a gradient magnetic field coil configured to form a gradient magnetic field in the measurement area; a transmission coil configured to transmit a transmission pulse toward a subject in the measurement area; a detection coil configured to detect a nuclear magnetic resonance signal generated in the subject by transmission of the transmission pulse; and a generator configured to generate an MR image based on the nuclear magnetic resonance signal detected by the detection coil. The static magnetic field forming unit includes: a first magnetic pole and a second magnetic pole arranged so as to face each other with the measurement area interposed therebetween; a first coil configured to generate a magnetic flux; and a first holding member which holds the first magnetic pole and the second magnetic pole and in which a magnetic path for guiding the magnetic flux generated by the first coil to each of the first magnetic pole and the second magnetic pole is formed.

In this brain measurement apparatus, when generating an MR image of the subject in the measurement area, a static magnetic field is formed in the measurement area by the static magnetic field forming unit. In the static magnetic field forming unit, a magnetic flux generated in the first coil is guided to the first magnetic pole and the second magnetic pole, which are arranged so as to face each other with the measurement area interposed therebetween, by the magnetic path formed in the first holding member. As a result, a static magnetic field is formed between the first magnetic pole and the second magnetic pole in the measurement area. Thus, in this brain measurement apparatus, a static magnetic field is formed by using a pair of magnetic poles arranged with the measurement area interposed therebetween. Therefore, in this brain measurement apparatus, it is possible to reduce the power consumption.

In the brain measurement apparatus according to the present disclosure, the first holding member may include: a first main body portion that extends along a first direction in which the first magnetic pole and the second magnetic pole face each other; a first extending portion that extends from one end of the first main body portion along a second direction crossing the first direction; and a second extending portion that extends from the other end of the first main body portion along the second direction. The first magnetic pole may be connected to and held by the first extending portion. The second magnetic pole may be connected to and held by the second extending portion. The first coil may be provided so as to be wound around the first main body portion. In this manner, by connecting the first magnetic pole and the second magnetic pole to the first extending portion and the second extending portion extending in one direction from both ends of the first main body portion of the first holding member, respectively, and providing the first coil in the first main body portion to guide the magnetic flux to each of the first magnetic pole and the second magnetic pole, it is possible to form a more uniform static magnetic field in the measurement area.

In the brain measurement apparatus according to the present disclosure, the first coil may be provided in the first main body portion so as to be symmetrical with respect to a reference line along the second direction, which is a line passing through a midpoint between the first magnetic pole and the second magnetic pole in the first direction. In this case, since the path length from the first coil to the first magnetic pole and the path length from the first coil to the second magnetic pole are made equal, the uniformity of the static magnetic field formed in the measurement area is further improved.

In the brain measurement apparatus according to the present disclosure, the first extending portion may include a first bent portion that is bent toward the second magnetic pole at an end portion of the first extending portion opposite to the first main body portion. The second extending portion may include a second bent portion that is bent toward the first magnetic pole at an end portion of the second extending portion opposite to the first main body portion. The first magnetic pole may have a circular shape when viewed from the first direction, and be connected to and held at a distal end of the first bent portion at a center of the circular shape. The second magnetic pole may have a circular shape when viewed from the first direction and be connected to and held at a distal end of the second bent portion at a center of the circular shape. In this case, since the magnetic flux from the first coil is guided to the center of each of the first magnetic pole and the second magnetic pole, the uniformity of the static magnetic field formed in the measurement area is further improved.

In the brain measurement apparatus according to the present disclosure, the first extending portion and the second extending portion may extend linearly along the second direction. The first magnetic pole may be connected to and held at a distal end of the first extending portion at an outer edge of the first magnetic pole on a side of the first extending portion. The second magnetic pole may be connected to and held at a distal end of the second extending portion at an outer edge of the second magnetic pole on a side of the second extending portion. In this case, since the magnetic path from the first coil to each of the first magnetic pole and the second magnetic pole can be made shorter, it is possible to improve the magnetic field strength of the static magnetic field formed in the measurement area.

In the brain measurement apparatus according to the present disclosure, the static magnetic field forming unit may include: a second coil for generating a magnetic flux; and a second holding member in which a magnetic path for guiding the magnetic flux generated by the second coil to each of the first magnetic pole and the second magnetic pole is formed. The second holding member may include: a second main body portion that extends along the first direction; a third extending portion that linearly extends from one end of the second main body portion along the second direction; and a fourth extending portion that linearly extends from the other end of the second main body portion along the second direction. A distal end of the third extending portion may be connected to an outer edge of the first magnetic pole on a side of the third extending portion. A distal end of the fourth extending portion may be connected to an outer edge of the second magnetic pole on a side of the fourth extending portion. The second coil may be provided so as to be wound around the second main body portion. In this case, coils are arranged on both sides of the first magnetic pole and the second magnetic pole and the magnetic flux is guided from the coils to the first magnetic pole and the second magnetic pole. Therefore, the uniformity of the static magnetic field formed in the measurement area is further improved.

In the brain measurement apparatus according to the present disclosure, a size of the first magnetic pole and a size of the second magnetic pole when viewed from a direction in which the first magnetic pole and the second magnetic pole face each other may be larger than a distance between the first magnetic pole and the second magnetic pole. In this case, in the area between the first magnetic pole and the second magnetic pole, an area on the center side where a more uniform static magnetic field is formed can be selectively used.

According to the present disclosure, it is possible to provide a brain measurement apparatus capable of reducing power consumption.

DETAILED DESCRIPTION

Figure 1:
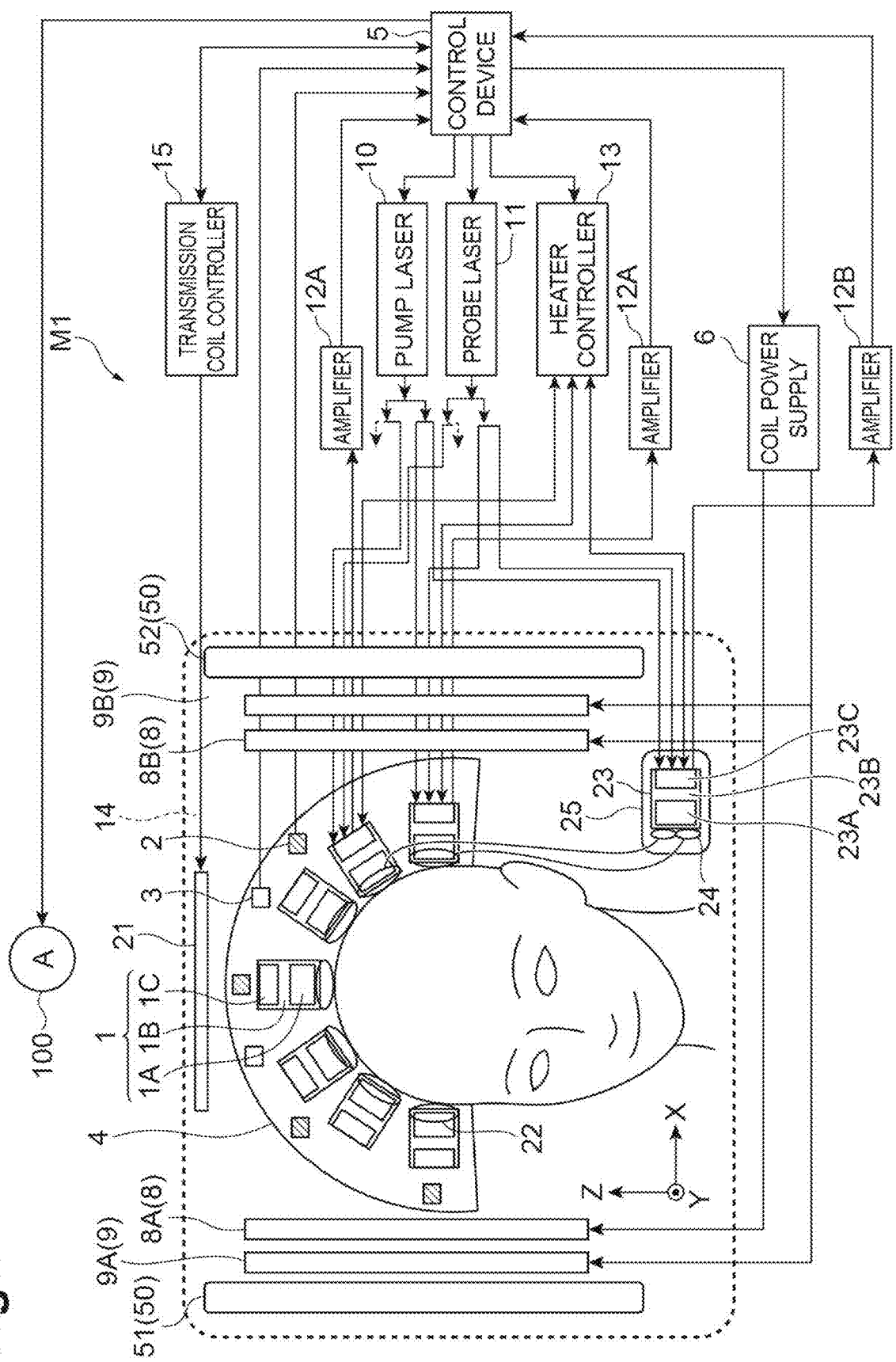
FIG. 1 is a schematic diagram showing a brain measurement apparatus according to an embodiment.

Hereinafter, a brain measurement apparatus and a brain measurement method according to an embodiment will be described with reference to the diagrams. In the description of the diagrams, the same elements or equivalent elements may be denoted by the same reference numerals, and the repeated description thereof may be omitted. In addition, each figure may show a Cartesian coordinate system defined by the X axis, the Y axis, and the Z axis. In the following description, a direction approximately parallel to the central axis of the head of the subject is defined as a Z-axis direction and directions perpendicular to the Z axis and perpendicular to each other are defined as an X-axis direction and a Y-axis direction.

FIG. 1 is a schematic diagram showing a brain measurement apparatus according to an embodiment. As shown in FIG. 1, a brain measurement apparatus M1 is an apparatus for acquiring the position and direction of an equivalent current dipole moment vector when a magnetic field generation source generated by the neural activity in the subject's brain is assumed as the equivalent current dipole moment vector and acquiring a magnetic resonance (MR) image of the subject. The brain measurement apparatus M1 includes multiple optically pumped magnetometer (OPM) modules 1, multiple magnetic sensors for geomagnetic field cancellation 2, multiple magnetic sensors for active shield 3, a non-magnetic frame 4, a pair of gradient magnetic field nulling coils 8 (geomagnetic field nulling coils), a pair of active shield coils 9, a static magnetic field forming unit 50, a transmission coil 21, a receive coil 22 (detection coil), an OPM module 23, and an output coil 24. In addition, the brain measurement apparatus M1 includes a control device (generator) 5, a coil power supply 6, a pump laser 10, a probe laser 11, amplifiers 12A and 12B, a heater controller 13, an electromagnetic shield 14, a transmission coil controller 15, and a power supply unit 100.

Each OPM module 1 includes an optically pumped magnetometer 1A, a heat insulating material 1B, and a read circuit 1C. The multiple OPM modules 1 are arranged at predetermined intervals along the scalp, for example. The optically pumped magnetometer 1A is a sensor that measures a brain's magnetic field by using optical pumping, and has a sensitivity of, for example, about 10 fT to 10 pT. The heat insulating material 1B prevents heat transfer of the optically pumped magnetometer 1A. The read circuit 1C is a circuit for acquiring the detection result of the optically pumped magnetometer 1A. The optically pumped magnetometer 1A emits pump light to a cell containing alkali metal vapor to excite the alkali metal.

The excited alkali metal is in a spin polarization state, and when this receives magnetic field, the inclination of the electron spin polarization axis of the alkali metal atom changes according to the magnetic field. The inclination of the electron spin polarization axis is detected by probe light emitted separately from the pump light. In addition, the optically pumped magnetometer 1A is configured such that a predetermined bias magnetic field is applied in the emission direction of the pump light so as to be sensitive to a magnetic field having a frequency included in the range of 0 to 200 Hz. The read circuit 1C receives probe light passing through the alkali metal vapor by a photodiode and acquires the detection result. The read circuit 1C outputs the detection result to the amplifier 12A.

The optically pumped magnetometer 1A may be, for example, an axial gradiometer. The axial gradiometer has a measurement region and a reference region in a direction perpendicular to the scalp (measurement location) of the subject and coaxially. The measurement region is, for example, a location closest to the scalp of the subject among locations where the axial gradiometer measures the brain's magnetic field. The reference region is, for example, a location away from the measurement region by a predetermined distance (for example, 3 cm) in a direction away from the scalp of the subject, among locations where the axial gradiometer measures the brain's magnetic field.

The axial gradiometer outputs the respective measurement results in the measurement region and the reference region to the amplifier 12A. Here, when common mode noise is included, its influence is shown in each of the output result of the measurement region and the output result of the reference region. Common mode noise is removed by acquiring the difference between the output result of the measurement region and the output result of the reference region. By removing the common mode noise, the optically pumped magnetometer 1A can obtain a sensitivity of about 10 fT/√Hz, for example, when performing measurement in a magnetic noise environment of 1 pT.

The magnetic sensor for geomagnetic field cancellation 2 is a sensor that measures a magnetic field relevant to the geomagnetic field at a position corresponding to the optically pumped magnetometer 1A, and is, for example, a flux gate sensor having a sensitivity of about 1 nT to 100 µT. The position corresponding to the optically pumped magnetometer 1A is a position around (near) the region where the optically pumped magnetometer 1A is arranged. The magnetic sensor for geomagnetic field cancellation 2 may be provided so as to correspond to the optically pumped magnetometer 1A in a one-to-one manner, or may be provided so as to correspond in a one-to-many manner (one magnetic sensor for geomagnetic field cancellation 2 for multiple optically pumped magnetometers 1A).

The magnetic sensor for geomagnetic field cancellation 2 measures, for example, geomagnetic field and a gradient magnetic field of the geomagnetic field (hereinafter, may be simply referred to as "gradient magnetic field") as magnetic fields relevant to the geomagnetic field, and outputs the measured value to the control device 5. The measured value of the magnetic sensor for geomagnetic field cancellation 2 can be expressed by a vector having a direction and a magnitude. The magnetic sensor for geomagnetic field cancellation 2 may continuously perform measurement and output at predetermined time intervals.

The magnetic sensor for active shield 3 is a sensor that measures a fluctuating magnetic field at a position corresponding to the optically pumped magnetometer 1A, and is, for example, an optically pumped magnetometer having a sensitivity of about 100 fT to 10 nT and different from the optically pumped magnetometer 1A. The position corresponding to the optically pumped magnetometer 1A is a position around (near) the region where the optically pumped magnetometer 1A is arranged. The magnetic sensor for active shield 3 may be provided so as to correspond to the optically pumped magnetometer 1A in a one-to-one manner, or may be provided so as to correspond in a one-to-many manner (one magnetic sensor for active shield 3 for the multiple optically pumped magnetometers 1A).

The magnetic sensor for active shield 3 measures a magnetic field of a noise (AC) component of, for example, 200 Hz or less as a fluctuating magnetic field, and outputs the measured value to the control device 5. The measured value of the magnetic sensor for active shield 3 can be expressed by a vector having a direction and a magnitude. The magnetic sensor for active shield 3 may continuously perform measurement and output at predetermined time intervals.

The non-magnetic frame 4 is a frame that covers the entire scalp of the subject whose brain's magnetic field is to be measured, and is formed of a non-magnetic material such as graphite whose relative magnetic permeability is close to 1 and accordingly does not affect the magnetic field distribution. The non-magnetic frame 4 can be, for example, a helmet-type frame that surrounds the entire scalp of the subject and is attached to the head of the subject. The multiple optically pumped magnetometers 1A are fixed to the non-magnetic frame 4 so as to be close to the scalp of the subject. In addition, the magnetic sensor for geomagnetic field cancellation 2 is fixed to the non-magnetic frame 4 so that a magnetic field relevant to the geomagnetic field at the position of each of the multiple optically pumped magnetometers 1A can be measured, and the magnetic sensor for active shield 3 is fixed to the non-magnetic frame 4 so that a fluctuating magnetic field at the position of each of the multiple optically pumped magnetometers 1A can be measured.

Since a change in the magnetic field strength according to the position of the fluctuating magnetic field is smaller than that in the case of the static magnetic field, a smaller number of magnetic sensors for active shield 3 than the number of magnetic sensors for geomagnetic field cancellation 2 may be fixed to the non-magnetic frame 4. In addition, the receive coil 22 for detecting a nuclear magnetic resonance signal for MR image measurement is fixed to the scalp side of the subject of the multiple optically pumped magnetometers 1A inside the non-magnetic frame 4. The receive coil 22 detects the nuclear magnetic resonance signal of the proton, which will be described later, and converts the nuclear magnetic resonance signal into an electric current. In order to improve the detection sensitivity of the nuclear magnetic resonance signal, it is preferable that the receive coil 22 is provided on the side of the optically pumped magnetometer 1A close to the scalp of the head of the subject.

The transmission coil 21 is a coil for emitting an RF pulse (transmission pulse) having a predetermined frequency (for example, about 300 kHz) to the head of the subject during MRI measurement. The transmission coil 21 is arranged above the head of the subject outside the non-magnetic frame 4, for example. The output coil 24 is electrically connected to both ends of the receive coil 22 through a cable, and receives a current flowing through both ends of the receive coil 22, converts the current into a magnetic signal again, and outputs the magnetic signal.

Similar to the OPM module 1, the OPM module 23 includes an optically pumped magnetometer 23A, a heat insulating material 23B, and a read circuit 23C. The OPM module 23 is housed in, for example, a magnetic shield 25 that shields a static magnetic field, which will be described later, outside the non-magnetic frame 4 together with the output coil 24. The magnetic shield 25 is formed of, for example, mu-metal having a relative magnetic permeability of more than 1.

The optically pumped magnetometer 23A is a sensor that measures a magnetic signal using optical pumping. In addition, the optically pumped magnetometer 23A is configured such that a predetermined bias magnetic field is applied in the emission direction of pump light so as to be sensitive to a magnetic field having a frequency included in the range of 20 kHz to 500 kHz. For example, a bias magnetic field of about 40 µT is applied so as to be sensitive to the frequency of 300 kHz of the electromagnetic wave emitted by the proton. The read circuit 23C outputs the detection result of the optically pumped magnetometer 23A to the amplifier 12B.

Figure 2:
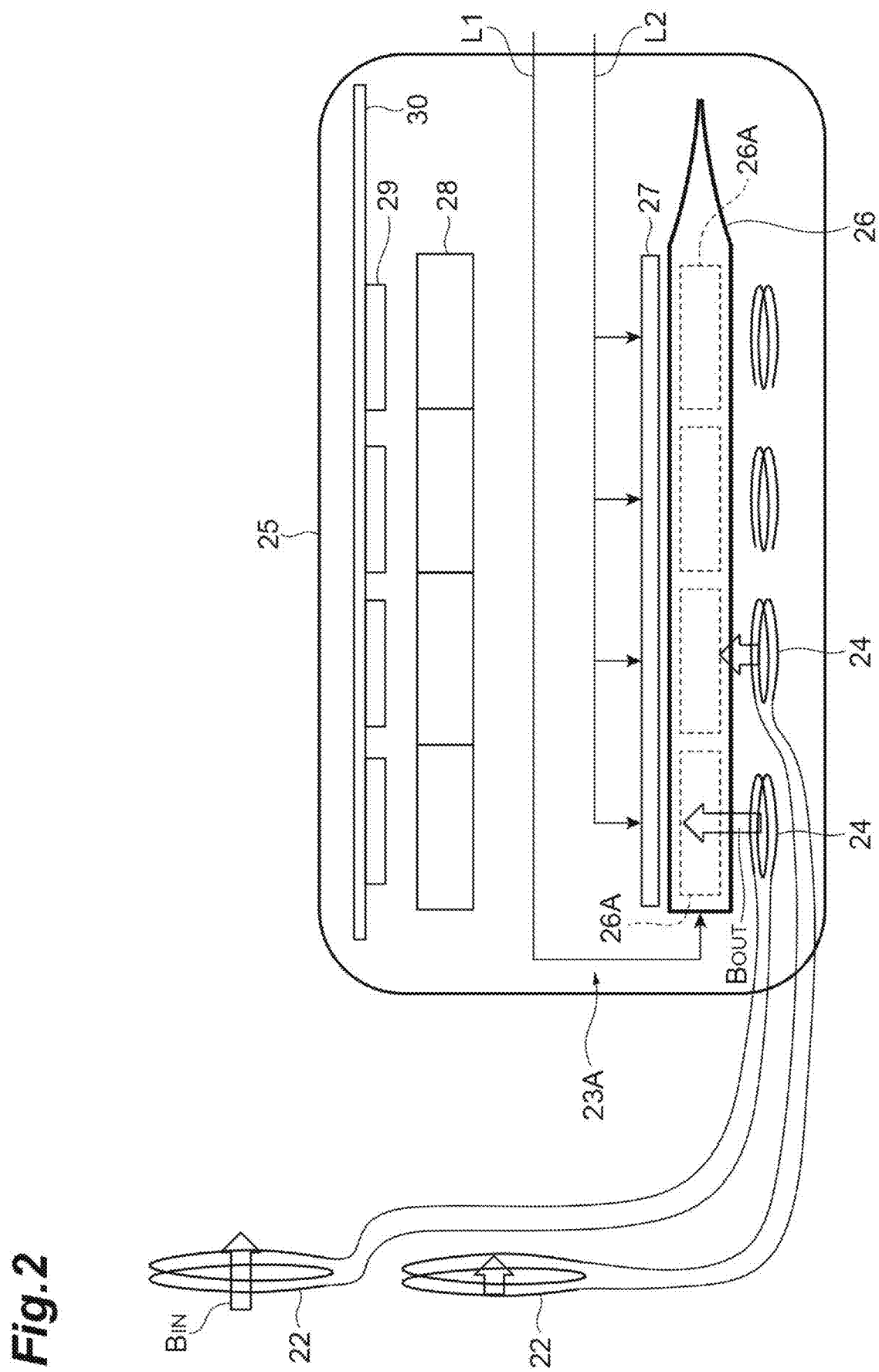
FIG. 2 is a diagram showing a specific example of the configuration of an OPM module shown in FIG. 1.

FIG. 2 shows a specific example of the configuration of the OPM module shown in FIG. 1. As shown in FIG. 2, the optically pumped magnetometer 23A includes a longitudinal cell 26 filled with a gas containing an alkali metal whose direction of polarization changes with a magnetic field to be measured, a heater 27 that heats the entire cell 26 to a predetermined temperature (for example, 180°), a polarization beam splitter 28, and a photodetector 29. Pump light L1 is introduced into the cell 26 from the outside along the longitudinal direction of the inside of the cell 26. In addition, along a direction perpendicular to the longitudinal direction, probe light L2 from the outside is branched and emitted to multiple crossing regions 26A (for example, four crossing regions 26A) divided in the longitudinal direction.

The polarization angle of the probe light L2 transmitted through the crossing regions 26A is detected by the polarization beam splitter 28 and the photodetector 29 provided corresponding to each of the crossing regions 26A. That is, the polarization beam splitter 28 separates the probe light L2 into two linearly polarized components perpendicular to each other, and the photodetector 29 detects the intensities of the two linearly polarized components using two built-in photodiodes (PDs) and detects the polarization angle of the probe light L2 based on the ratio of the detected intensities. A circuit board 30 is further provided in the OPM module 23. Through the read circuit 23C in the circuit board 30, the polarization angle of the probe light L2 detected for each crossing region 26A is output.

In the magnetic shield 25, the output coil 24 is fixed so as to face each crossing region 26A of the cell 26 in the OPM module 23 having the above-described configuration. With such a configuration, a magnetic signal $B_{OUT}$ generated by the output coil 24 based on the electromagnetic field $B_{OUT}$ detected by the receive coil 22 is detected based on the polarization angle of the probe light L2 that changes according to the inclination of the electron spin polarization axis of the alkali metal atom. Here, in the example of FIG. 2, the number of divided crossing regions 26A is four, but may be changed to any number. In addition, multiple cells 26 may be provided in parallel, so that the crossing regions 26A are arrayed in a two-dimensional manner (for example, 4×4=16).

When measuring the brain's magnetic field, the control device 5 determines currents for various coils based on the measured values output from the magnetic sensor for geomagnetic field cancellation 2 and the magnetic sensor for active shield 3, and outputs a control signal for outputting each of the currents to the coil power supply 6 and the power supply unit 100. Based on the measured values of the multiple magnetic sensors for geomagnetic field cancellation 2, the control device 5 determines a current for the static magnetic field forming unit 50 and the gradient magnetic field nulling coil 8 so as to generate a magnetic field for canceling a magnetic field relevant to the geomagnetic field. The details of the static magnetic field forming unit 50 will be described later. In addition, based on the measured values of the multiple magnetic sensors for active shield 3, the control device 5 determines a current for the active shield coil 9 so as to generate a magnetic field for canceling a fluctuating magnetic field. The control device 5 outputs a control signal corresponding to the determined current to the coil power supply 6.

Specifically, the control device 5 determines a current for the static magnetic field forming unit 50 so that the average value of the measured values of the multiple magnetic sensors for geomagnetic field cancellation 2 approaches zero (as a result, a magnetic field opposite to the geomagnetic field at the position of the optically pumped magnetometer 1A and having approximately the same magnitude as the geomagnetic field is generated). The control device 5 outputs a control signal (control signal for static magnetic field cancellation) corresponding to the determined current of the static magnetic field forming unit 50 to the power supply unit 100.

In addition, the control device 5 determines a current for the gradient magnetic field nulling coil 8 so that the deviation from the average value of the measured values of the multiple magnetic sensors for geomagnetic field cancellation 2 is minimized (as a result, a magnetic field opposite to the gradient magnetic field at the position of the optically pumped magnetometer 1A and having approximately the same magnitude as the gradient magnetic field is generated). The control device 5 outputs a control signal (control signal for static magnetic field cancellation) corresponding to the determined current of the gradient magnetic field nulling coil 8 to the coil power supply 6.

In addition, the control device 5 determines a current for the active shield coil 9 so that the average value of the measured values of the multiple magnetic sensors for active shield 3 approaches zero (as a result, a magnetic field opposite to the fluctuating magnetic field at the position of the optically pumped magnetometer 1A and having approximately the same magnitude as the fluctuating magnetic field is generated). The control device 5 outputs a control signal (control signal for fluctuating magnetic field cancellation) corresponding to the determined current of the active shield coil 9 to the coil power supply 6.

In addition, the control device 5 obtains information regarding the magnetic field detected by the optically pumped magnetometer 1A by using the signal output from the amplifier 12A. When the optically pumped magnetometer 1A is an axial gradiometer, the control device 5 may remove the common mode noise by acquiring the difference between the output result of the measurement region and the output result of the reference region. In addition, the control device 5 may control operations such as the emission timing and the emission time of the pump laser 10 and the probe laser 11.

In addition, when measuring the MR image, the control device 5 determines a current to be supplied to each of the static magnetic field forming unit 50 and the gradient magnetic field nulling coil 8, which operate as coils for applying the static magnetic field and the gradient magnetic field, respectively, and outputs a control signal for outputting the current to the coil power supply 6 and the power supply unit 100. That is, the control device 5 determines a current flowing through the static magnetic field forming unit 50 so that an X-axis direction magnetic field having a predetermined strength (for example, 7 mT) is applied to the head of the subject as a static magnetic field. In addition, the control device 5 selectively determines an X-axis direction magnetic field gradient ($dB_X/dX$), a Y-axis direction magnetic field gradient ($dB_X/dY$), and a Z-axis direction magnetic field gradient ($dB_X/dZ$) as a gradient magnetic field to determine a current flowing through the gradient magnetic field nulling coil 8. Therefore, a slicing position in the MR image can be determined, and the position within the slice surface can be encoded by phase encoding and frequency encoding. In addition, when measuring the MR image, the control device 5 outputs a control signal so that no current is supplied to the active shield coil 9 for removing low-frequency noise.

In addition, when measuring the MR image, the control device 5 outputs a control signal, which is for controlling electric power supplied to the transmission coil 21, to the transmission coil controller 15, so that control to emit a transmission pulse having a predetermined frequency (for example, about 300 kHz when the strength of the static magnetic field is 7 mT) to the head of the subject is performed. As a result, protons on the slice surface (surface selected by the static magnetic field and the gradient magnetic field) resonate to tilt the spin. Thereafter, the control device 5 controls the electric power of the transmission coil 21 to be turned off. As a result, it is possible to acquire the MR image by measuring how the spin returns based on the output of the OPM module 23. More specifically, the control device 5 measures the nuclear magnetic resonance signal from the proton by encoding the position with frequency and phase using a known spin echo sequence or gradient echo sequence, and converts the measurement result into an MR image using FFT.

The control device 5 is physically configured to include a memory such as a RAM and a ROM, a processor (arithmetic circuit) such as a CPU, a communication interface, and a storage unit such as a hard disk. Examples of the control device 5 include a personal computer, a cloud server, a smartphone, and a tablet terminal. The control device 5 functions by executing a program stored in the memory on the CPU of the computer system.

The coil power supply 6 outputs a predetermined current to each of the gradient magnetic field nulling coil 8, and the active shield coil 9 in response to the control signal output from the control device 5. In addition, the power supply unit 100 outputs a current to the static magnetic field forming unit 50 in response to the control signal relevant to the static magnetic field forming unit 50. In addition, the coil power supply 6 outputs a current to the gradient magnetic field nulling coil 8 in response to the control signal relevant to the gradient magnetic field nulling coil 8. The coil power supply 6 outputs a current to the active shield coil 9 in response to the control signal relevant to the active shield coil 9.

The transmission coil controller 15 is electrically connected to the transmission coil 21, and supplies electric power to the transmission coil 21 in response to the control signal output from the control device 5 so that a transmission pulse having a predetermined frequency is emitted.

The static magnetic field forming unit 50 is also configured to cancel the magnetic field of the geomagnetic field among the magnetic fields relevant to the geomagnetic field at the position of the optically pumped magnetometer 1A. The static magnetic field forming unit 50 generates a magnetic field according to the current supplied from the power supply unit 100 to cancel the geomagnetic field. Here, the static magnetic field forming unit 50 has a pair of first magnetic pole 51 and second magnetic pole 52, which will be described in detail later. The pair of first magnetic pole 51 and second magnetic pole 52 are arranged with the optically pumped magnetometer 1A interposed therebetween (for example, on the left and right of the subject). The pair of first magnetic pole 51 and second magnetic pole 52 generate a magnetic field, which is opposite to the geomagnetic field at the position of the optically pumped magnetometer 1A and has approximately the same magnitude as the geomagnetic field, according to the current supplied from the power supply unit 100. The direction of the magnetic field is, for example, the X-axis direction, the Y-axis direction, and the Z-axis direction. The geomagnetic field at the position of the optically pumped magnetometer 1A is canceled by a magnetic field generated by the first magnetic pole 51 and the second magnetic pole 52, the magnetic field being opposite to the geomagnetic field and having approximately the same magnitude as the geomagnetic field.

In this manner, the static magnetic field forming unit 50 can cancel the geomagnetic field at the position of the optically pumped magnetometer 1A. In addition, the static magnetic field forming unit 50 has a role of generating a static magnetic field in the X-axis direction during MR image measurement. The static magnetic field forming unit 50 generates a static magnetic field having a predetermined strength according to the current supplied from the power supply unit 100.

The gradient magnetic field nulling coil 8 is a coil for cancelling the gradient magnetic field among the magnetic fields relevant to the geomagnetic field at the position of the optically pumped magnetometer 1A. The gradient magnetic field nulling coil 8 generates a magnetic field according to the current supplied from the coil power supply 6 to cancel the gradient magnetic field. The gradient magnetic field nulling coil 8 has, for example, a pair of gradient magnetic field nulling coils 8A and 8B. The pair of gradient magnetic field nulling coils 8A and 8B are arranged with the optically pumped magnetometer 1A interposed therebetween (for example, on the left and right of the subject). The pair of gradient magnetic field nulling coils 8A and 8B generate a magnetic field, which is opposite to the gradient magnetic field at the position of the optically pumped magnetometer 1A and has approximately the same magnitude as the gradient magnetic field, according to the current supplied from the coil power supply 6. The direction of the magnetic field is, for example, the X-axis direction, the Y-axis direction, and the Z-axis direction. The gradient magnetic field at the position of the optically pumped magnetometer 1A is canceled by a magnetic field generated by the gradient magnetic field nulling coil 8, the magnetic field being opposite to the gradient magnetic field and having approximately the same magnitude as the gradient magnetic field.

In this manner, the gradient magnetic field nulling coil 8 cancels the gradient magnetic field at the position of the optically pumped magnetometer 1A. In addition, the gradient magnetic field nulling coil 8 has a role as a gradient magnetic field coil for generating a gradient magnetic field during MR image measurement. The gradient magnetic field nulling coil 8 generates a gradient magnetic field having a selective gradient in the X-axis direction, the Y-axis direction, and the Z-axis direction according to the current supplied from the coil power supply 6.

The active shield coil 9 is a coil for cancelling the fluctuating magnetic field at the position of the optically pumped magnetometer 1A. The active shield coil 9 generates a magnetic field according to the current supplied from the coil power supply 6 to cancel the fluctuating magnetic field. The active shield coil 9 has, for example, a pair of active shield coils 9A and 9B. The pair of active shield coils 9A and 9B are arranged with the optically pumped magnetometer 1A interposed therebetween (for example, on the left and right of the subject). The pair of active shield coils 9A and 9B generate a magnetic field, which is opposite to the fluctuating magnetic field at the position of the optically pumped magnetometer 1A and has approximately the same magnitude as the fluctuating magnetic field, according to the current supplied from the coil power supply 6. The direction of the magnetic field is, for example, the X-axis direction, the Y-axis direction, and the Z-axis direction. The fluctuating magnetic field at the position of the optically pumped magnetometer 1A is canceled by a magnetic field generated by the active shield coil 9, the magnetic field being opposite to the fluctuating magnetic field and having approximately the same magnitude as the fluctuating magnetic field. In this manner, the active shield coil 9 cancels the fluctuating magnetic field at the position of the optically pumped magnetometer 1A.

The pump laser 10 is a laser device that generates pump light. The pump light emitted from the pump laser 10 is incident on each of the multiple optically pumped magnetometers 1A and the optically pumped magnetometers 23A by fiber branching. The probe laser 11 is a laser device that generates probe light. The probe light emitted from the probe laser 11 is incident on each of the multiple optically pumped magnetometers 1A and the optically pumped magnetometers 23A by fiber branching.

The amplifier 12A is a device or circuit that amplifies an output result signal from the OPM module 1 (specifically, the read circuit 1C) and outputs the signal to the control device 5. The amplifier 12B is a device or circuit that amplifies an output result signal from the OPM module 23 (specifically, the read circuit 23C) and outputs the signal to the control device 5.

The heater controller 13 is a temperature adjusting device connected to a heater for heating the cell of the optically pumped magnetometer 1A and the cell of the optically pumped magnetometer 23A and a thermocouple (not shown) for measuring the temperature of each cell. The heater controller 13 adjusts the temperature of each cell by receiving the temperature information of the cell from the thermocouple and adjusting the heating of the heater based on the temperature information.

The electromagnetic shield 14 is a shield member for shielding high-frequency (for example, 10 kHz or higher) electromagnetic noise. For example, the electromagnetic shield 14 is formed of a mesh woven with metal threads, a non-magnetic metal plate such as aluminum, or the like. The electromagnetic shield 14 is arranged so as to surround the OPM modules 1 and 23, the transmission coil 21, the receive coil 22, the output coil 24, the magnetic sensor for geomagnetic field cancellation 2, the magnetic sensor for active shield 3, the non-magnetic frame 4, the static magnetic field forming unit 50, the gradient magnetic field nulling coil 8, and the active shield coil 9. The electromagnetic shield 14 can prevent noise in the 300 kHz band, which is a measurement frequency, from entering the receive coil 22 to increase the noise during MR image measurement. In addition, it is possible to prevent high-frequency noise from entering the optically pumped magnetometer 1A to cause an unstable operation during the measurement of the brain's magnetic field.

Figure 3:
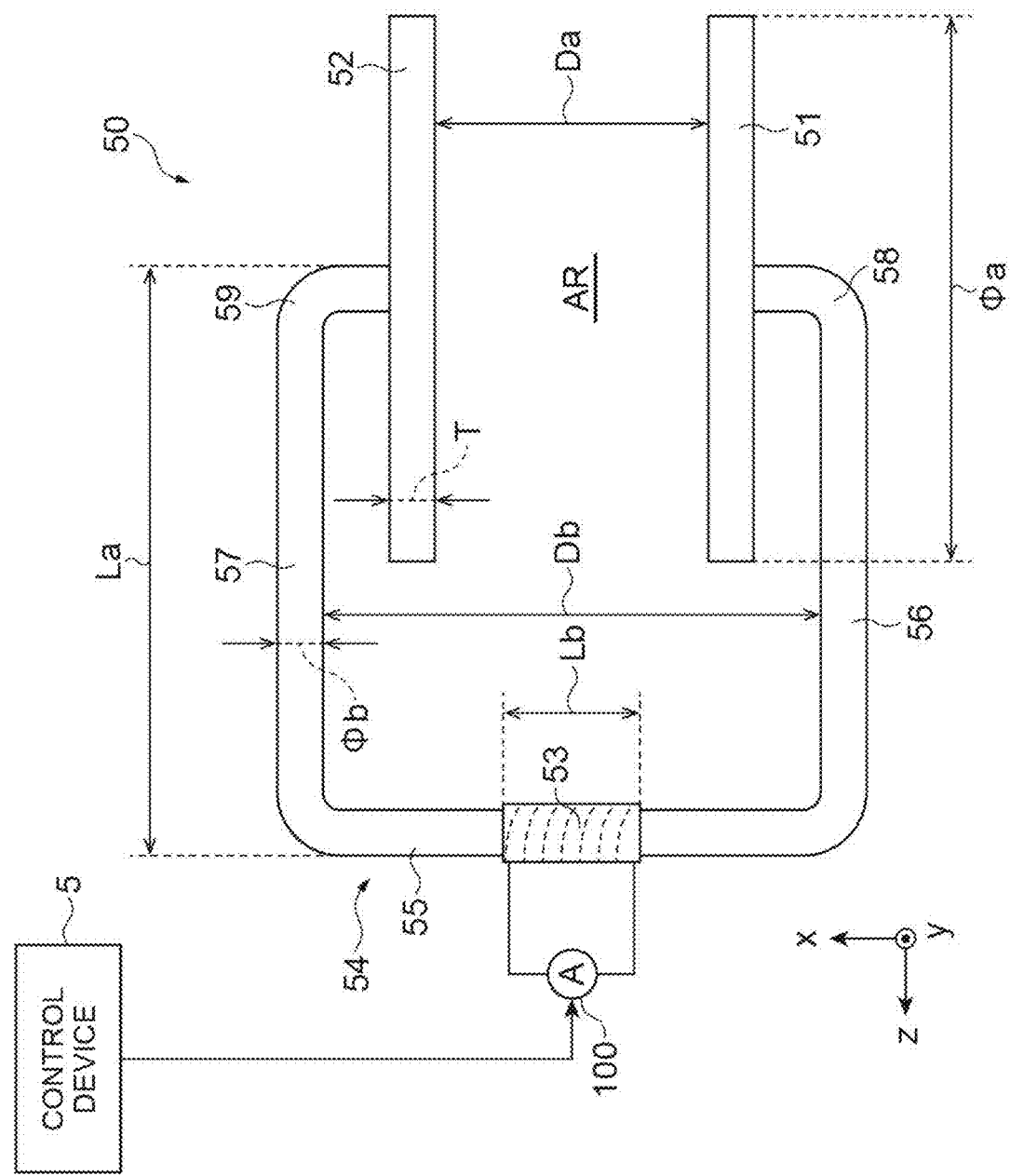
FIG. 3 is a side view showing a static magnetic field forming unit shown in FIG. 1.

Subsequently, the details of the static magnetic field forming unit 50 will be described. FIG. 3 is a side view showing the static magnetic field forming unit shown in FIG. 1. As shown in FIG. 3, the static magnetic field forming unit 50 has the first magnetic pole 51, the second magnetic pole 52, a first coil 53, and a first holding member 54. Here, the first magnetic pole 51 and the second magnetic pole 52 are arranged so as to be separated from each other and face each other along the X-axis direction. As a result, a static magnetic field is formed between the first magnetic pole 51 and the second magnetic pole 52 during MR image measurement. Therefore, the area between the first magnetic pole 51 and the second magnetic pole 52 is a measurement area AR. In other words, the first magnetic pole 51 and the second magnetic pole 52 are arranged so as to face each other with the measurement area AR interposed therebetween.

Referring to FIG. 1, the gradient magnetic field nulling coil 8 and the active shield coil 9 are arranged between the first magnetic pole 51 and the second magnetic pole 52, at least when viewed from the Y direction. Therefore, while the static magnetic field forming unit 50 is for forming a static magnetic field in the measurement area AR, the gradient magnetic field nulling coil 8 is a gradient magnetic field coil for forming a gradient magnetic field in the measurement area AR during MR image measurement. In addition, the transmission coil 21 is arranged so as to face the measurement area AR, and is for transmitting a transmission pulse toward the subject in the measurement area AR during MR image measurement. The receive coil 22 is for detecting the nuclear magnetic resonance signal generated in the subject by transmitting the transmission pulse during MR image measurement. In addition, the control device (generator) 5 generates an MR image based on the nuclear magnetic resonance signal detected by the receive coil 22.

Subsequently, FIG. 3 is referred to. The first coil 53 receives the electric power supplied from the power supply unit 100 to generate a magnetic flux. The first coil 53 is provided so as to be wound around the first holding member 54. The first holding member 54 holds the first magnetic pole 51 and the second magnetic pole 52, and forms a magnetic path for guiding the magnetic flux generated by the first coil 53 to each of the first magnetic pole 51 and the second magnetic pole 52. As a result, a magnetic field is generated between the first magnetic pole 51 and the second magnetic pole 52 (measurement area AR).

The first holding member 54 includes a first main body portion 55 extending along the X-axis direction (first direction) in which the first magnetic pole 51 and the second magnetic pole 52 face each other, a first extending portion 56 extending from one end of the first main body portion 55 along the Z-axis direction (second direction) crossing the X-axis direction, and a second extending portion 57 extending from the other end of the first main body portion 55 along the Y-axis direction. As an example, the first extending portion 56 and the second extending portion 57 are substantially parallel to each other. The first magnetic pole 51 is connected to and held by the first extending portion 56, and the second magnetic pole 52 is connected to and held by the second extending portion 57.

More specifically, the first extending portion 56 includes a first bent portion 58 that is bent toward the second magnetic pole 52 at an end portion of the first extending portion 56 opposite to the first main body portion 55, and the second extending portion 57 includes a second bent portion 59 that is bent toward the first magnetic pole 51 at an end portion of the second extending portion 57 opposite to the first main body portion 55. As a result, the first holding member 54 is configured in a substantially C shape as a whole. The first magnetic pole 51 is connected to and held at the distal end of the first bent portion 58, and the second magnetic pole 52 is connected to and held at the distal end of the second bent portion 59.

Here, in particular, the first magnetic pole 51 and the second magnetic pole 52 each have a disk shape, and are connected to the first bent portion 58 and the second bent portion 59, respectively, at the approximate center of the circular shape. Therefore, the measurement area AR formed between the first magnetic pole 51 and the second magnetic pole 52 can be formed in a substantially columnar shape, for example. The first holding member 54 has a rod shape with a circular cross section as an example. The first magnetic pole 51, the second magnetic pole 52, and the first holding member 54 are formed in a solid shape by using a magnetic material (for example, steel) having a high magnetic permeability so that a magnetic flux easily passes therethrough.

Here, the number of first coils 53 is one, and the first coil 53 is provided at the center of the first main body portion 55. However, the multiple first coils 53 may be provided. In this case, the multiple first coils 53 may be provided in the first main body portion 55 so as to be symmetrical with respect to the reference line along the Z-axis direction, which is a line passing through the midpoint between the first magnetic pole 51 and the second magnetic pole 52 in the X-axis direction. The number of turns of the first coil 53 is, for example, 1000 Turn, and a current of about 3 A flows through the first coil 53. In this case, the power consumption can be about 50 W.

Here, the size of the first magnetic pole 51 and the size of the second magnetic pole 52 when viewed from a direction (X-axis direction) in which the first magnetic pole 51 and the second magnetic pole 52 face each other are larger than a distance Da between the first magnetic pole 51 and the second magnetic pole 52. As an example, the distance Da between the first magnetic pole 51 and the second magnetic pole 52 is about 300 mm, and the diameter φa of each of the first magnetic pole 51 and the second magnetic pole 52 is about 600 mm That is, in this example, the sizes of the first magnetic pole 51 and the second magnetic pole 52 are about twice the distance Da between the first magnetic pole 51 and the second magnetic pole 52. In addition, the thickness T of each of the first magnetic pole 51 and the second magnetic pole 52 is uniform as, for example, about 75 mm. However, the thickness T of each of the first magnetic pole 51 and the second magnetic pole 52 may not be uniform. As an example, the first magnetic pole 51 and the second magnetic pole 52 may be formed so as to be relatively thick in the vicinity of a peripheral portion. In this case, a decrease in the uniformity of the static magnetic field in the vicinity of the peripheral portion is suppressed, and the uniformity of the static magnetic field formed in the measurement area AR is further improved. In addition, in this example, the first magnetic pole 51 and the second magnetic pole 52 have the same shape.

The diameter φb of the first holding member 54 is, for example, about 50 mm to 100 mm, and as an example, about 75 mm. The length La of each of the first extending portion 56 and the second extending portion 57 is, for example, about 600 mm. In addition, a distance Db between the first extending portion 56 and the second extending portion 57 along the X-axis direction is about 600 mm. Therefore, the length La of each of the first extending portion 56 and the second extending portion 57, the diameter φa of each of the first magnetic pole 51 and the second magnetic pole 52, and the distance Db between the first extending portion 56 and the second extending portion 57 can be approximately the same. In addition, the length Lb of the range of the first main body portion 55 in which the first coil 53 is provided is, for example, about 150 mm.

Figure 4A:
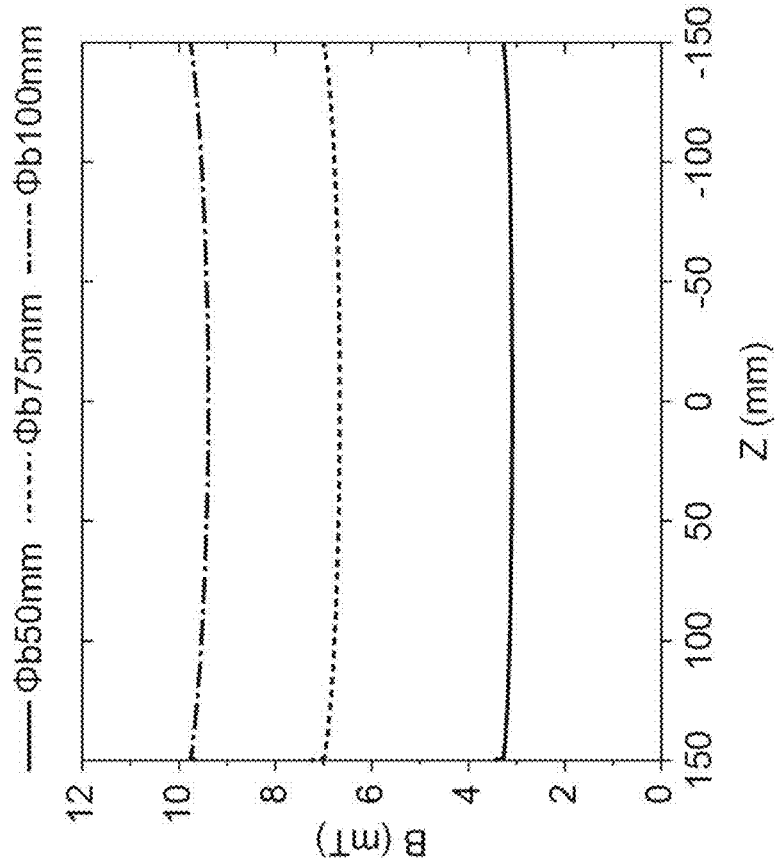
FIGS. 4A and 4B are graphs showing a magnetic flux density distribution due to a magnetic field formed by the static magnetic field forming unit.
Figure 4B:
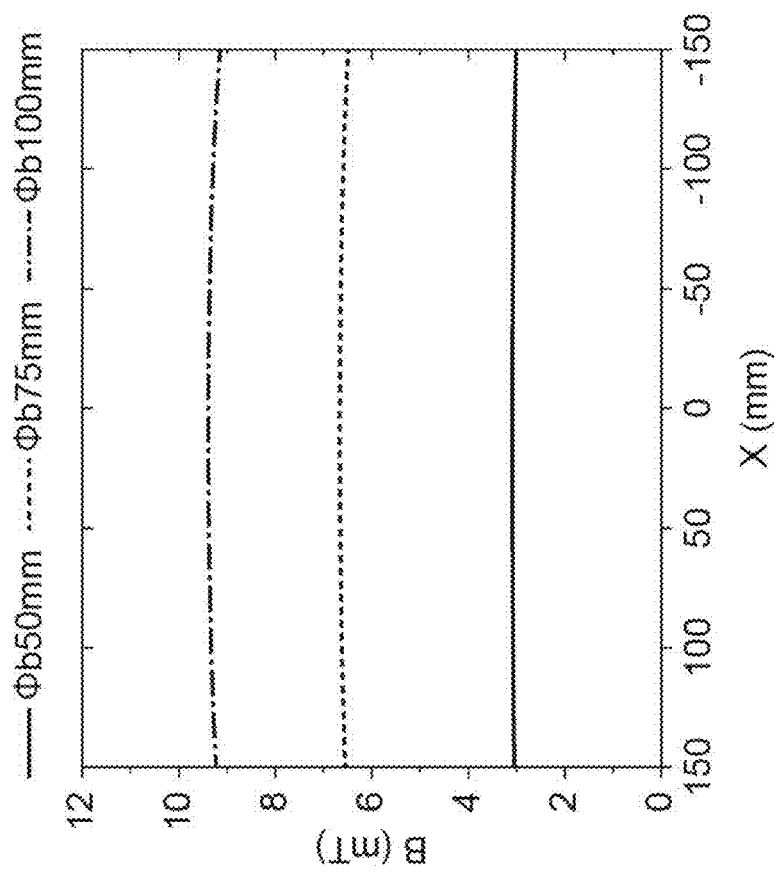

Subsequently, a magnetic field formed by the static magnetic field forming unit 50 configured as described above will be described. FIGS. 4A and 4B are graphs showing the magnetic flux density distribution of the measurement area due to the magnetic field formed by the static magnetic field forming unit. In FIG. 4A, the horizontal axis indicates a position in the X-axis direction, and in FIG. 4B, the horizontal axis indicates a position in the Z-axis direction. In each case, the center is 0. Therefore, in any of FIGS. 4A and 4B, the range of 0 mm to ±150 mm corresponds to a range of about 150 mm in the radial direction from the circular center of the first magnetic pole 51 and the second magnetic pole 52.

Figure 5:
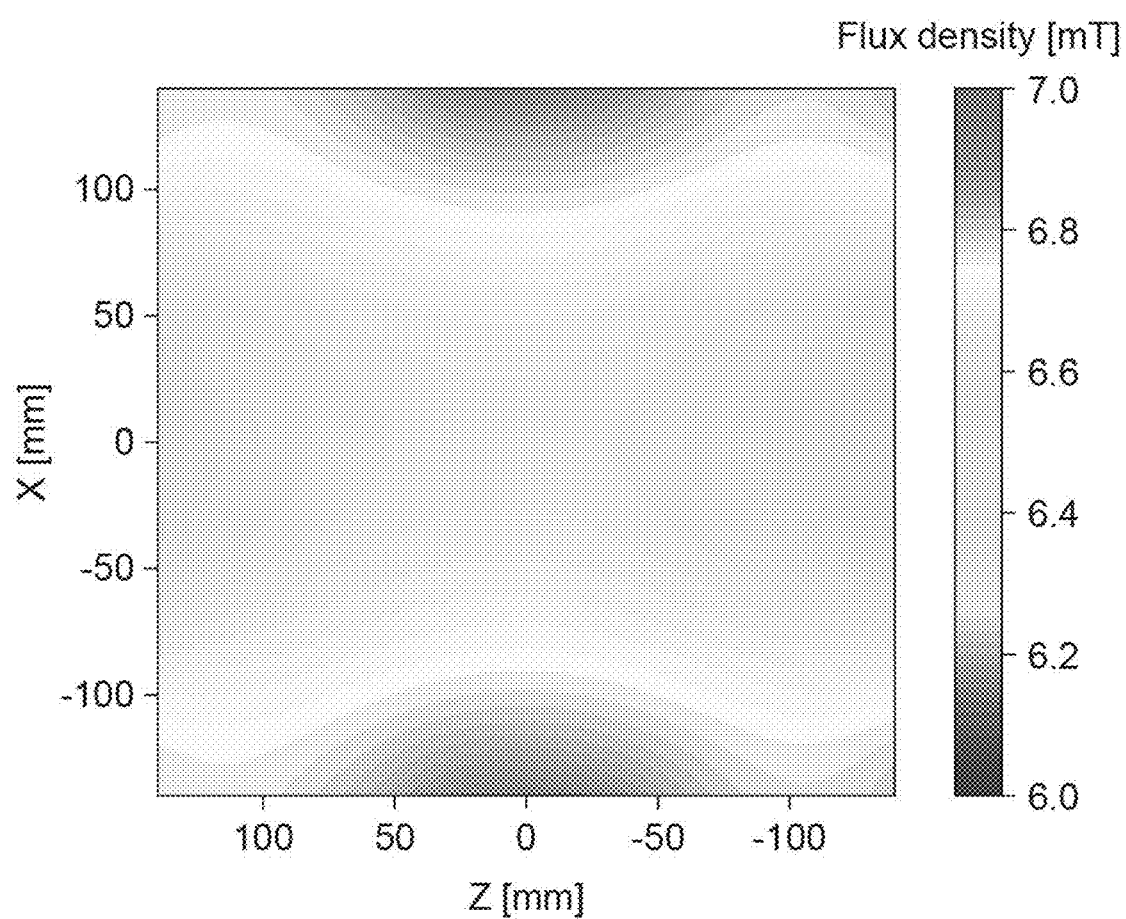
FIG. 5 is a graph showing a magnetic flux density distribution due to a magnetic field formed by the static magnetic field forming unit.
Figure 6:
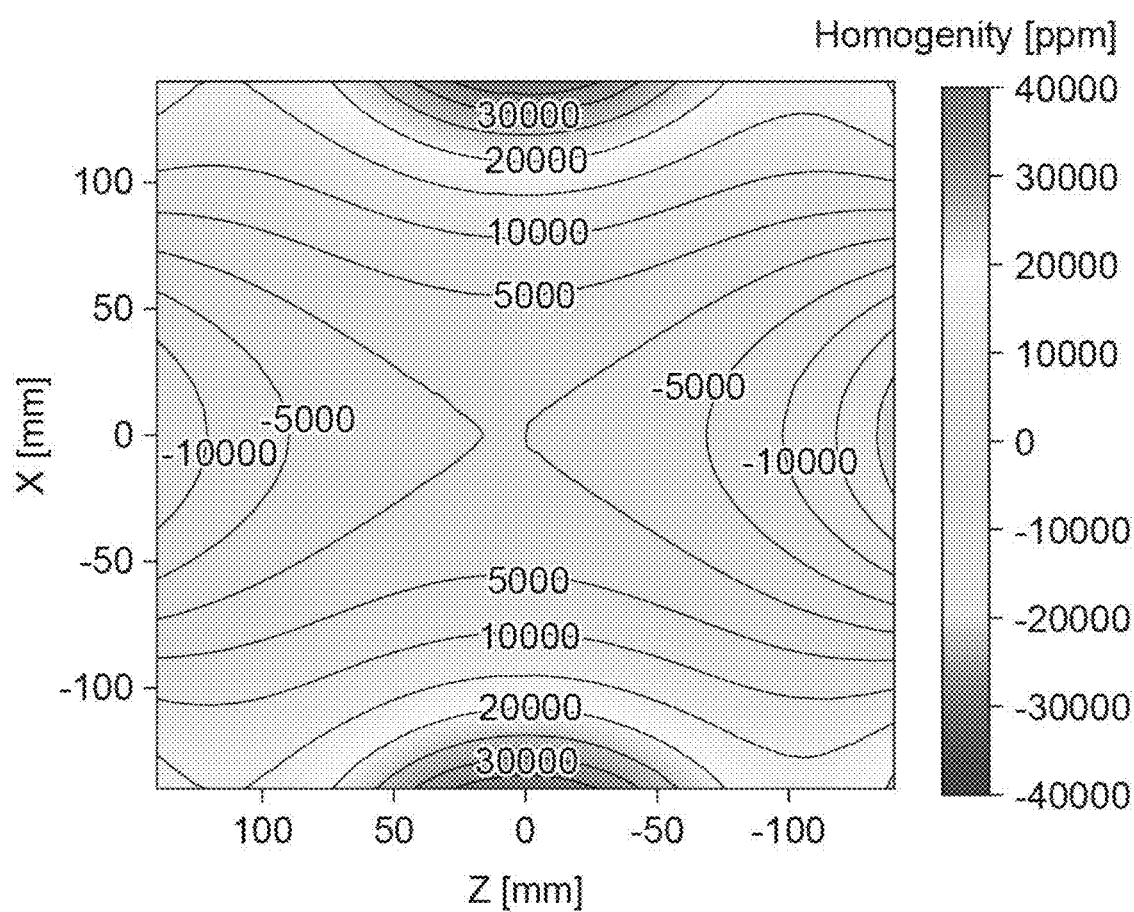
FIG. 6 is a graph showing a magnetic flux density distribution due to a magnetic field formed by the static magnetic field forming unit.

As shown in FIGS. 4A and 4B, according to the static magnetic field forming unit 50 configured as described above, it is understood that a uniform magnetic flux density distribution of about 3 mT when the diameter φb of the first holding member 54 is 50 mm, about 6.5 mT to 7 mT when the diameter φb is 75 mm, and about 9 mT when the diameter φb is 100 mm can be obtained in the XZ plane. In particular, as shown in FIGS. 5 and 6, when the diameter φb of the first holding member 54 is 75 mm, it is understood that an approximately uniform magnetic flux density distribution of 6.7 mT can be obtained in the range of at least about φ200 mm in the XZ plane in the measurement area AR.

Figure 7:
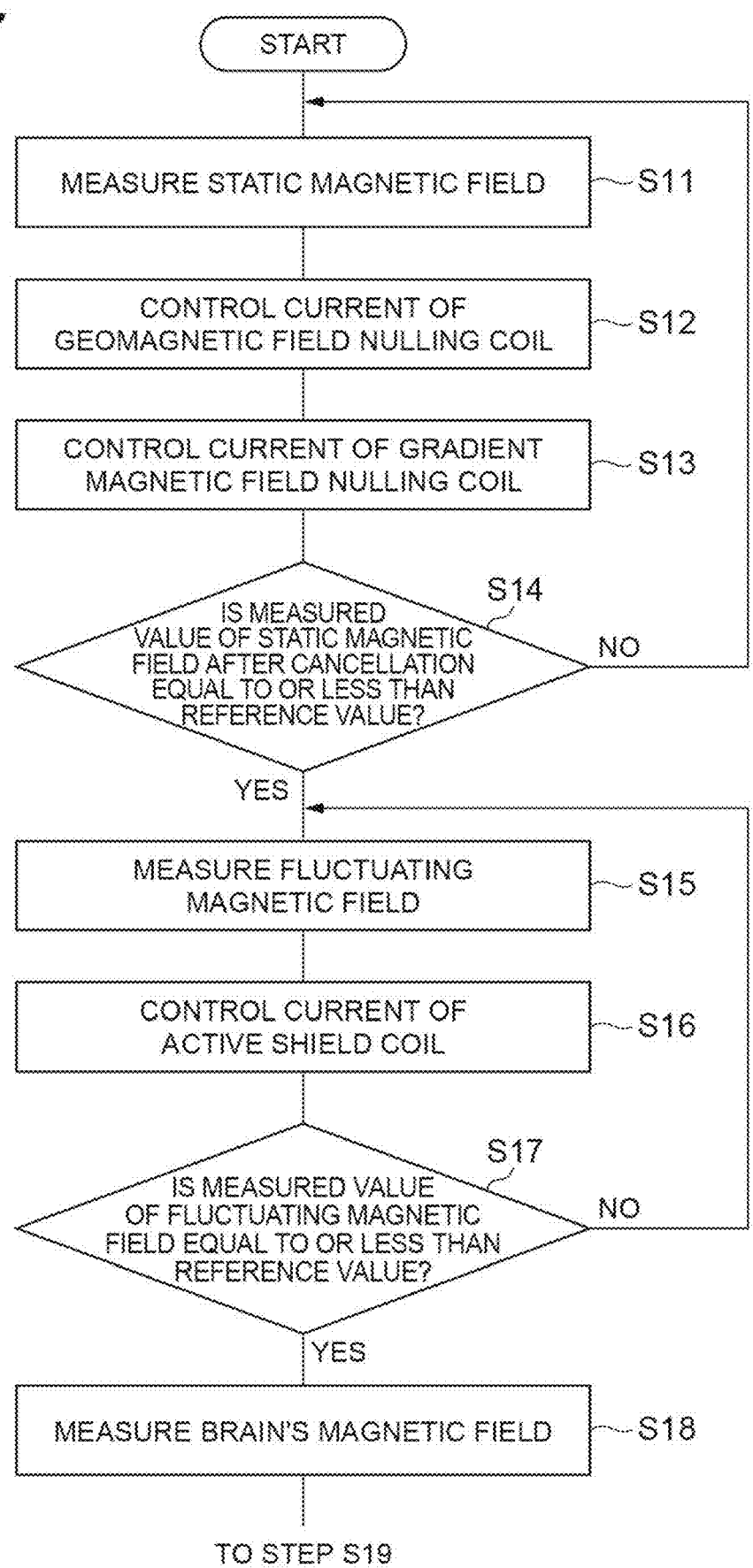
FIG. 7 is a flowchart showing one process of a brain measurement method according to an embodiment.
Figure 8:
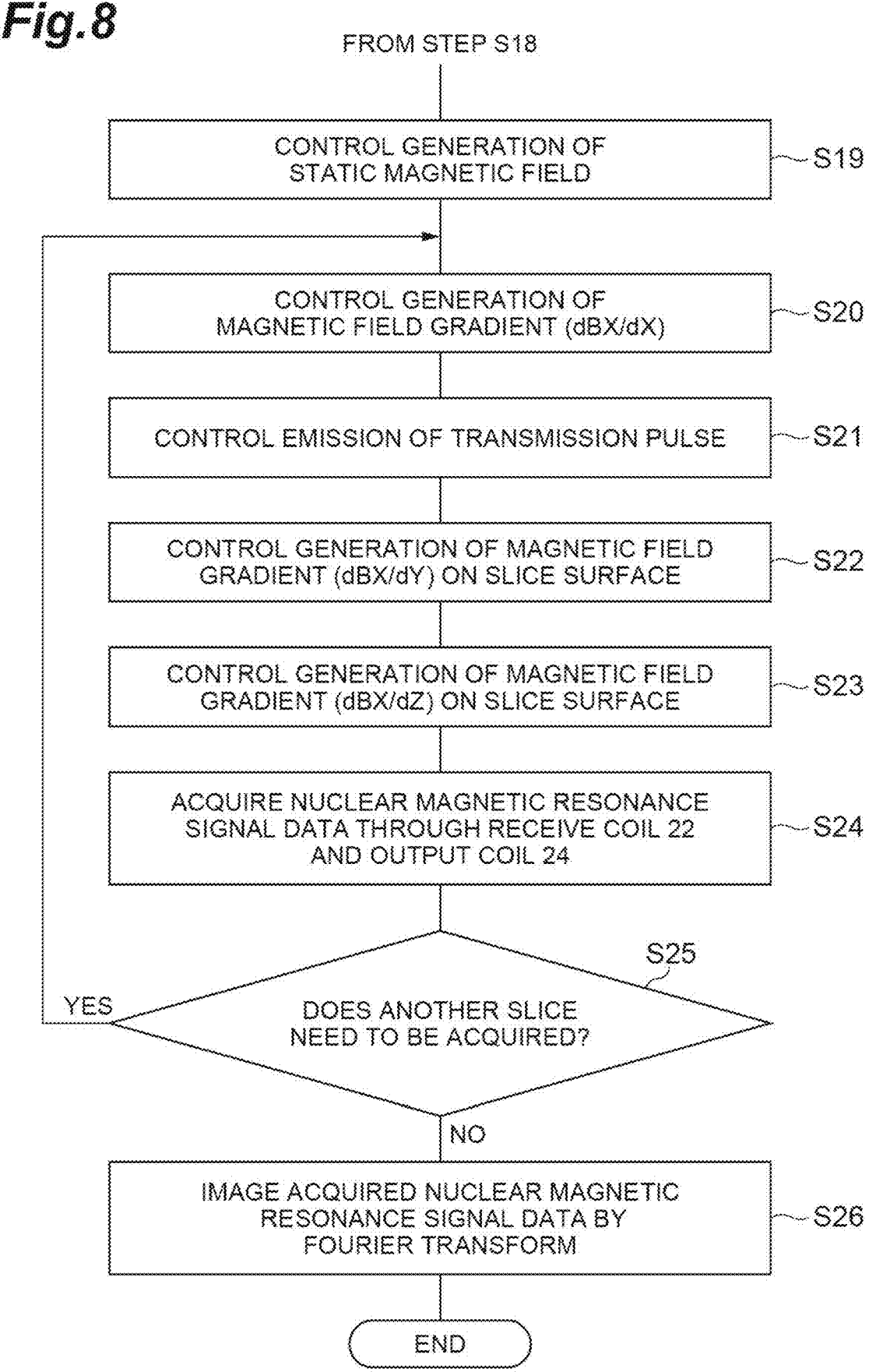
FIG. 8 is a flowchart showing one process of the brain measurement method according to an embodiment.

Subsequently, a brain measurement method according to an embodiment will be described with reference to FIGS. 7 and 8. FIGS. 7 and 8 are flowcharts showing one process of the brain measurement method according to the embodiment.

First, when the measurement of the brain's magnetic field starts with the non-magnetic frame 4 attached to the subject, the magnetic sensor for geomagnetic field cancellation 2 measures a magnetic field relevant to the geomagnetic field, which is a static magnetic field (step S11). The magnetic sensor for geomagnetic field cancellation 2 measures the geomagnetic field and the gradient magnetic field at each position of the optically pumped magnetometer 1A, and outputs the measured values to the control device 5.

The control device 5 and the coil power supply 6 control a current for the static magnetic field forming unit 50 (step S12). The control device 5 determines a current for the static magnetic field forming unit 50 (that is, the first coil 53) based on the measured value of the magnetic sensor for geomagnetic field cancellation 2 so that a magnetic field opposite to the geomagnetic field at the position of the optically pumped magnetometer 1A and having approximately the same magnitude as the geomagnetic field is generated. More specifically, the control device 5 determines a current for the static magnetic field forming unit 50 so that the average value of the measured values of the multiple magnetic sensors for geomagnetic field cancellation 2 approaches zero, for example. The control device 5 outputs a control signal corresponding to the determined current to the coil power supply 6. The power supply unit 100 outputs a predetermined current to the first coil 53 in response to the control signal output from the control device 5. The first coil 53 generates a magnetic flux according to the current supplied from the power supply unit 100. The magnetic flux generated by the first coil 53 is guided to the first magnetic pole 51 and the second magnetic pole 52 by the first holding member 54. As a result, a magnetic field is generated between the first magnetic pole 51 and the second magnetic pole 52. The geomagnetic field at the position of the optically pumped magnetometer 1A is canceled by a magnetic field generated by the first coil 53, the magnetic field being opposite to the geomagnetic field and having approximately the same magnitude as the geomagnetic field. In this manner, the static magnetic field forming unit 50 also functions as a geomagnetic field nulling coil for cancelling the magnetic field of the geomagnetic field.

The control device 5 and the coil power supply 6 control a current for the gradient magnetic field nulling coil 8 (step S13). The control device 5 determines a current for the gradient magnetic field nulling coil 8 based on the measured value of the magnetic sensor for geomagnetic field cancellation 2 so that a magnetic field opposite to the gradient magnetic field at the position of the optically pumped magnetometer 1A and having approximately the same magnitude as the gradient magnetic field is generated. More specifically, the control device 5 determines a current for the gradient magnetic field nulling coil 8 so that the deviation from the average value of the measured values of the multiple magnetic sensors for geomagnetic field cancellation 2 is minimized, for example. The control device 5 outputs a control signal corresponding to the determined current to the coil power supply 6. The coil power supply 6 outputs a predetermined current to the gradient magnetic field nulling coil 8 in response to the control signal output from the control device 5. The gradient magnetic field nulling coil 8 generates a magnetic field according to the current supplied from the coil power supply 6. The gradient magnetic field at the position of the optically pumped magnetometer 1A is canceled by a magnetic field generated by the gradient magnetic field nulling coil 8, the magnetic field being opposite to the gradient magnetic field and having approximately the same magnitude as the gradient magnetic field.

The control device 5 determines whether or not the measured value of the static magnetic field (magnetic field relevant to the geomagnetic field) after the cancellation is equal to or less than the reference value (step S14). The measured value of the static magnetic field after the cancellation is a value measured by the magnetic sensors for geomagnetic field cancellation 2 after the static magnetic field is canceled by the static magnetic field forming unit 50 and the gradient magnetic field nulling coil 8. The reference value is the magnitude of the magnetic field in which the optically pumped magnetometer 1A normally operates, and can be set to, for example, 1 nT. If the measured value of the static magnetic field is not equal to or less than the reference value ("NO" in step S14), the process returns to step S11. If the measured value of the static magnetic field is equal to or less than the reference value ("YES" in step S14), the process proceeds to step S15.

The magnetic sensor for active shield 3 measures a fluctuating magnetic field (step S15). The magnetic sensor for active shield 3 measures a fluctuating magnetic field at each position of the optically pumped magnetometer 1A and outputs the measured value to the control device 5.

The control device 5 and the coil power supply 6 control a current for the active shield coil 9 (step S16). The control device 5 determines a current for the active shield coil 9 based on the measured value of the magnetic sensor for active shield 3 so that a magnetic field opposite to the fluctuating magnetic field at the position of the optically pumped magnetometer 1A and having approximately the same magnitude as the fluctuating magnetic field is generated. More specifically, the control device 5 determines a current for the active shield coil 9 so that the average value of the measured values of the multiple magnetic sensors for active shield 3 approaches zero, for example. The control device 5 outputs a control signal corresponding to the determined current to the coil power supply 6. The coil power supply 6 outputs a predetermined current to the active shield coil 9 in response to the control signal output from the control device 5. The active shield coil 9 generates a magnetic field according to the current supplied from the coil power supply 6. The fluctuating magnetic field at the position of the optically pumped magnetometer 1A is canceled by a magnetic field generated by the active shield coil 9, the magnetic field being opposite to the fluctuating magnetic field and having approximately the same magnitude as the fluctuating magnetic field.

The control device 5 determines whether or not the measured value of the fluctuating magnetic field after the cancellation is equal to or less than the reference value (step S17). The measured value of the fluctuating magnetic field after the cancellation is a value measured by the magnetic sensor for active shield 3 after the fluctuating magnetic field is canceled by the active shield coil 9. The reference value is a noise level at which the brain's magnetic field can be measured, and can be set to, for example, 1 pT. If the measured value of the fluctuating magnetic field is not less than or equal to the reference value ("NO" in step S17), the process returns to step S15. If the measured value of the fluctuating magnetic field is equal to or less than the reference value ("YES" in step S17), the process proceeds to step S18.

The optically pumped magnetometer 1A measures a brain's magnetic field (step S18). The control device 5 outputs the acquired measurement result to a predetermined output destination. The predetermined output destination may be a memory of the control device 5, a storage device of the control device 5 such as a hard disk, an output device of the control device 5 such as a display, or an external device such as a terminal device connected through a communication interface. Since the static magnetic field (magnetic field relevant to the geomagnetic field) and the fluctuating magnetic field at the position of the optically pumped magnetometer 1A are canceled so as to be equal to or less than a predetermined reference value, the optically pumped magnetometer 1A can measure the brain's magnetic field in a state in which the influence of the static magnetic field (magnetic field relevant to the geomagnetic field) and the influence of the fluctuating magnetic field are avoided. As described above, the control device 5 is also a generator for generating the brain's magnetic field distribution of the subject based on the detection result of the brain's magnetic field by the optically pumped magnetometer 1A.

Moving to FIG. 8, when MR image measurement starts subsequently with the non-magnetic frame 4 attached to the subject, the control device 5 controls the generation of a static magnetic field in the X-axis direction in the head of the subject by determining a current to be supplied to the static magnetic field forming unit 50 (that is, the first coil 53) for applying the static magnetic field and outputting a control signal to the power supply unit 100 (step S19). In this manner, the static magnetic field forming unit 50 also functions as a static magnetic field coil for applying a static magnetic field. Then, the control device 5 controls the generation of an X-axis direction magnetic field gradient ($dB_X/dX$) by determining a current to be supplied to the gradient magnetic field nulling coil 8 for generating the gradient magnetic field and outputting a control signal to the coil power supply 6 (step S20). At the same time, the control device 5 outputs a control signal, which is for controlling the electric power to be supplied to the transmission coil 21, to the transmission coil controller 15 to control the transmission pulse to be emitted to the head of the subject (step S21). As a result, protons on a predetermined slice surface are excited.

In addition, the control device 5 controls the generation of a Y-axis direction magnetic field gradient ($dB_X/dY$) on the slice surface by determining a current to be supplied to the gradient magnetic field nulling coil 8 for generating the gradient magnetic field and outputting a control signal to the coil power supply 6 (step S22). As a result, phase encoding is performed. Then, the control device 5 controls the generation of a Z-axis direction magnetic field gradient ($dB_X/dZ$) on the slice surface by determining a current to be supplied to the gradient magnetic field nulling coil 8 for generating the gradient magnetic field and outputting a control signal to the coil power supply 6 (step S23). As a result, frequency encoding is performed.

At the same time, a nuclear magnetic resonance signal from the proton is output from the OPM module 23 through the receive coil 22 and the output coil 24, and the control device 5 acquires the data of the nuclear magnetic resonance signal (step S24). Thereafter, the control device 5 determines whether or not to acquire nuclear magnetic resonance signal data regarding another slice surface (step S25). As a result of the determination, when nuclear magnetic resonance signal data regarding another slice surface is acquired ("YES" in step S25), the process returns to step S20. On the other hand, when nuclear magnetic resonance signal data regarding another slice surface is not acquired ("NO" in step S25), an MR image is acquired by Fourier-transforming the nuclear magnetic resonance signal data acquired so far (step S26). The control device 5 outputs the acquired MR image to a predetermined output destination. The predetermined output destination may be a memory of the control device 5, a storage device of the control device 5 such as a hard disk, an output device of the control device 5 such as a display, or an external device such as a terminal device connected through a communication interface. As described above, the control device 5 is also a generator that generates an MR image of the subject based on the nuclear magnetic resonance signal detected by the receive coil 22.

As described above, in the brain measurement apparatus M1, when generating the MR image of the subject in the measurement area AR, a static magnetic field is formed in the measurement area AR by the static magnetic field forming unit 50. In the static magnetic field forming unit 50, a magnetic flux generated in the first coil 53 is guided to the first magnetic pole 51 and the second magnetic pole 52, which are arranged so as to face each other with the measurement area AR interposed therebetween, by the magnetic path formed in the first holding member 54. As a result, a static magnetic field is formed between the first magnetic pole 51 and the second magnetic pole 52 in the measurement area AR. As described above, in the brain measurement apparatus M1, a static magnetic field is formed by using a pair of first magnetic pole 51 and second magnetic pole 52 that are arranged with the measurement area AR interposed therebetween. Therefore, in the brain measurement apparatus M1, the power consumption can be reduced by about 99% as compared with a case where a static magnetic field is formed by arranging an air core coil so as to surround the measurement area AR, for example.

In addition, in the brain measurement apparatus M1, the first holding member 54 includes the first main body portion 55 extending along the X-axis direction (first direction) in which the first magnetic pole 51 and the second magnetic pole 52 face each other, the first extending portion 56 extending from one end of the first main body portion 55 along the Z-axis direction (second direction) crossing the X-axis direction, and the second extending portion 57 extending from the other end of the first main body portion 55 along the Z-axis direction. The first magnetic pole 51 is connected to and held by the first extending portion 56, and the second magnetic pole 52 is connected to and held by the second extending portion 57. In addition, the first coil 53 is provided so as to be wound around the first main body portion 55. In this manner, by connecting the first magnetic pole 51 and the second magnetic pole 52 to the first extending portion 56 and the second extending portion 57 extending in one direction from both ends of the first main body portion 55 of the first holding member 54, respectively, and providing the first coil 53 in the first main body portion 55 to guide the magnetic flux to each of the first magnetic pole 51 and the second magnetic pole 52, it is possible to form a more uniform static magnetic field in the measurement area AR.

In addition, in the brain measurement apparatus M1, the first coil 53 is provided in the first main body portion 55 so as to be symmetrical with respect to the reference line along the Z-axis direction, which is a line passing through the midpoint between the first magnetic pole 51 and the second magnetic pole 52 in the X-axis direction. Therefore, since the path length from the first coil 53 to the first magnetic pole 51 and the path length from the first coil 53 to the second magnetic pole 52 are made equal, the uniformity of the static magnetic field formed in the measurement area AR is further improved.

In addition, in the brain measurement apparatus M1, the first extending portion 56 includes the first bent portion 58 that is bent toward the second magnetic pole 52 at the end portion of the first extending portion 56 opposite to the first main body portion 55, and the second extending portion 57 includes the second bent portion 59 that is bent toward the first magnetic pole 51 at the end portion of the second extending portion 57 opposite to the first main body portion 55. In addition, the first magnetic pole 51 has a circular shape when viewed from the X-axis direction, and is connected to and held at the distal end of the first bent portion 58 at the center of the circular shape. In addition, the second magnetic pole 52 has a circular shape when viewed from the X-axis direction, and is connected to and held at the distal end of the second bent portion 59 at the center of the circular shape. Therefore, since the magnetic flux from the first coil 53 is guided to the center of each of the first magnetic pole 51 and the second magnetic pole 52, the uniformity of the static magnetic field formed in the measurement area AR is further improved.

In addition, in the brain measurement apparatus M1, the size (for example, the diameter ϕa) of the first magnetic pole 51 and the size (for example, the diameter ϕa) of the second magnetic pole 52 when viewed from the direction (X-axis direction) in which the first magnetic pole 51 and the second magnetic pole 52 face each other are larger than the distance Da between the first magnetic pole 51 and the second magnetic pole 52. Therefore, in the area between the first magnetic pole 51 and the second magnetic pole 52, an area on the center side where a more uniform static magnetic field is formed can be selectively used.

In the above embodiment, one aspect of the present disclosure has been described. Therefore, the present disclosure is not limited to the disclosure contents described above, and can be arbitrarily modified. Subsequently, a modification example will be described.

Figure 9:
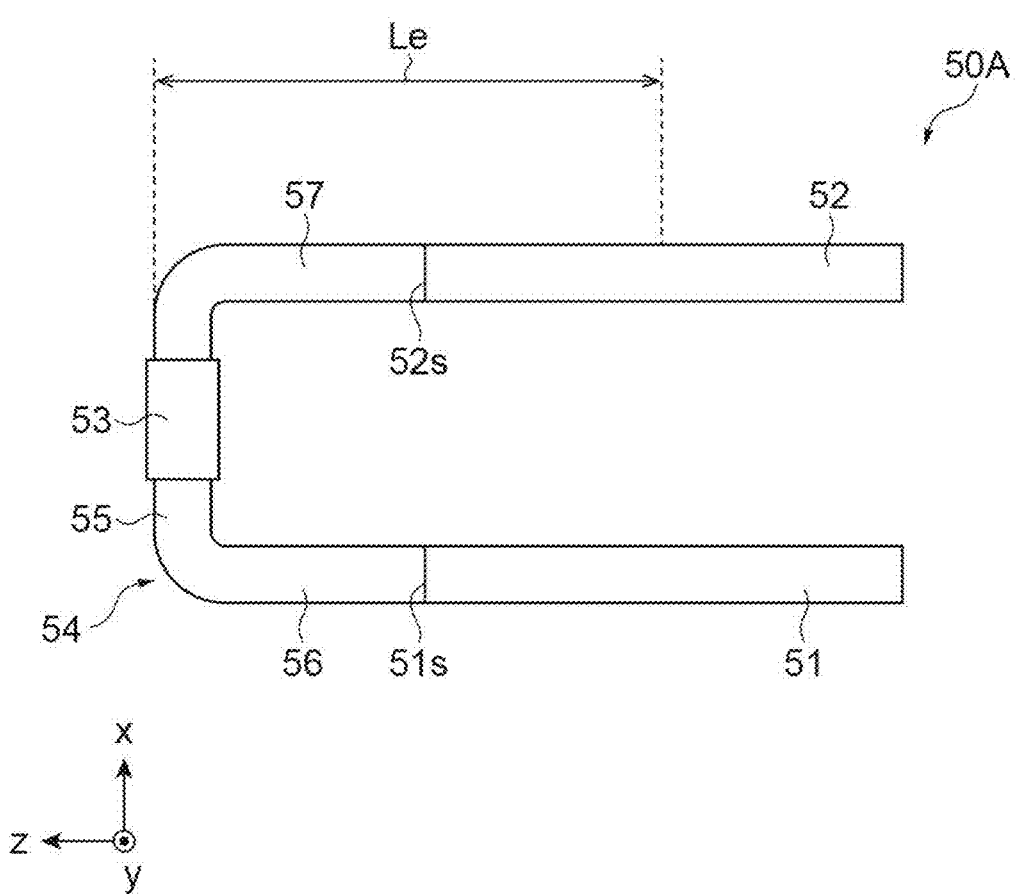
FIG. 9 is a side view showing a static magnetic field forming unit according to a modification example.

FIG. 9 is a side view showing a static magnetic field forming unit according to a modification example. A static magnetic field forming unit 50A shown in FIG. 9 is the same as the static magnetic field forming unit 50 according to the embodiment described above except for the connection between the first extending portion 56 and the first magnetic pole 51 and the connection between the second extending portion 57 and the second magnetic pole 52.

More specifically, in the static magnetic field forming unit 50A, the first extending portion 56 and the second extending portion 57 extend linearly along the Z-axis direction. In addition, the first magnetic pole 51 is connected to and held at the distal end of the first extending portion 56 at an outer edge 51s of the first magnetic pole 51 on the first extending portion 56 side. In addition, the second magnetic pole 52 is connected to and held at the distal end of the second extending portion 57 at an outer edge 52s of the second magnetic pole 52 on the second extending portion 57 side. In addition, the length Le from the center of each of the first magnetic pole 51 and the second magnetic pole 52 to the edge of each of the first extending portion 56 and the second extending portion 57 in the Z-axis direction is, for example, about 600 mm, and can be approximately the same as the size (for example, the diameter ϕa) of each of the first magnetic pole 51 and the second magnetic pole 52.

Figure 10:
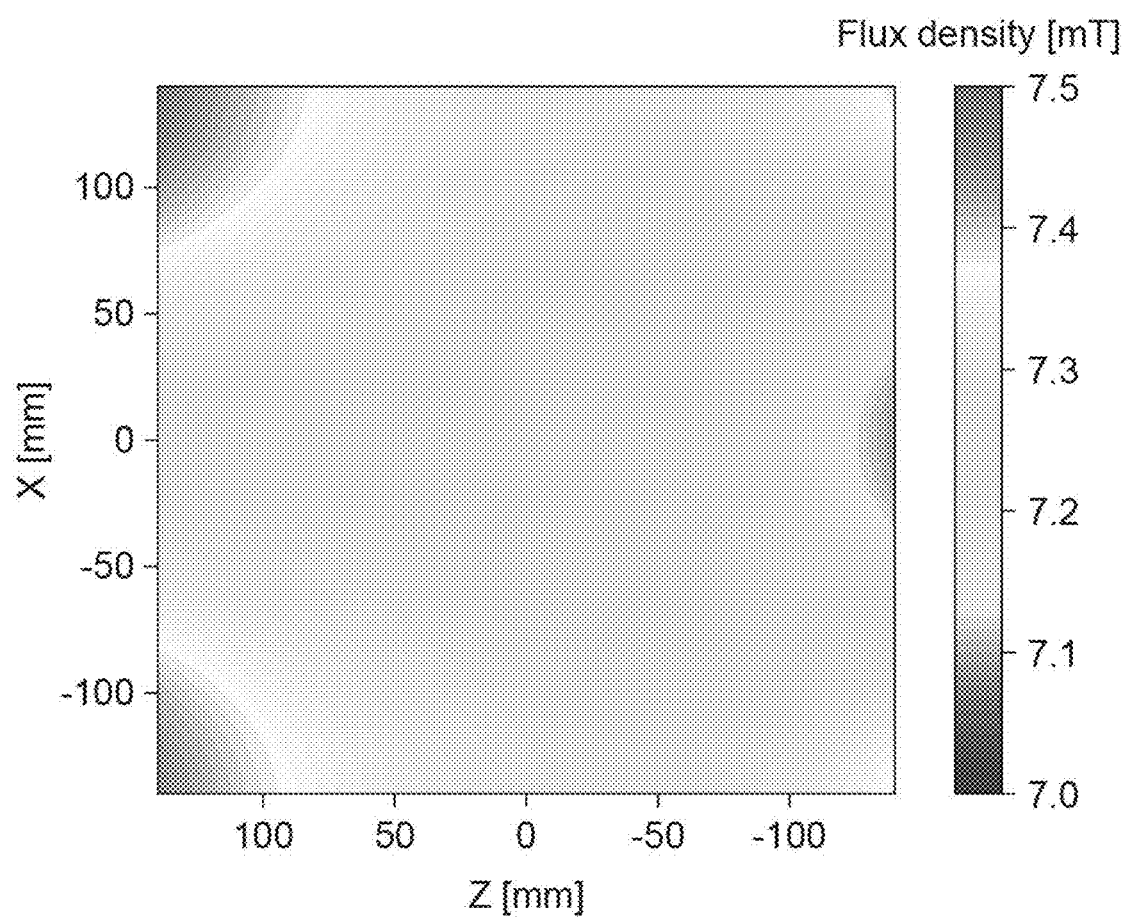
FIG. 10 is a graph showing a magnetic flux density distribution due to a magnetic field formed by the static magnetic field forming unit shown in FIG. 9.
Figure 11:
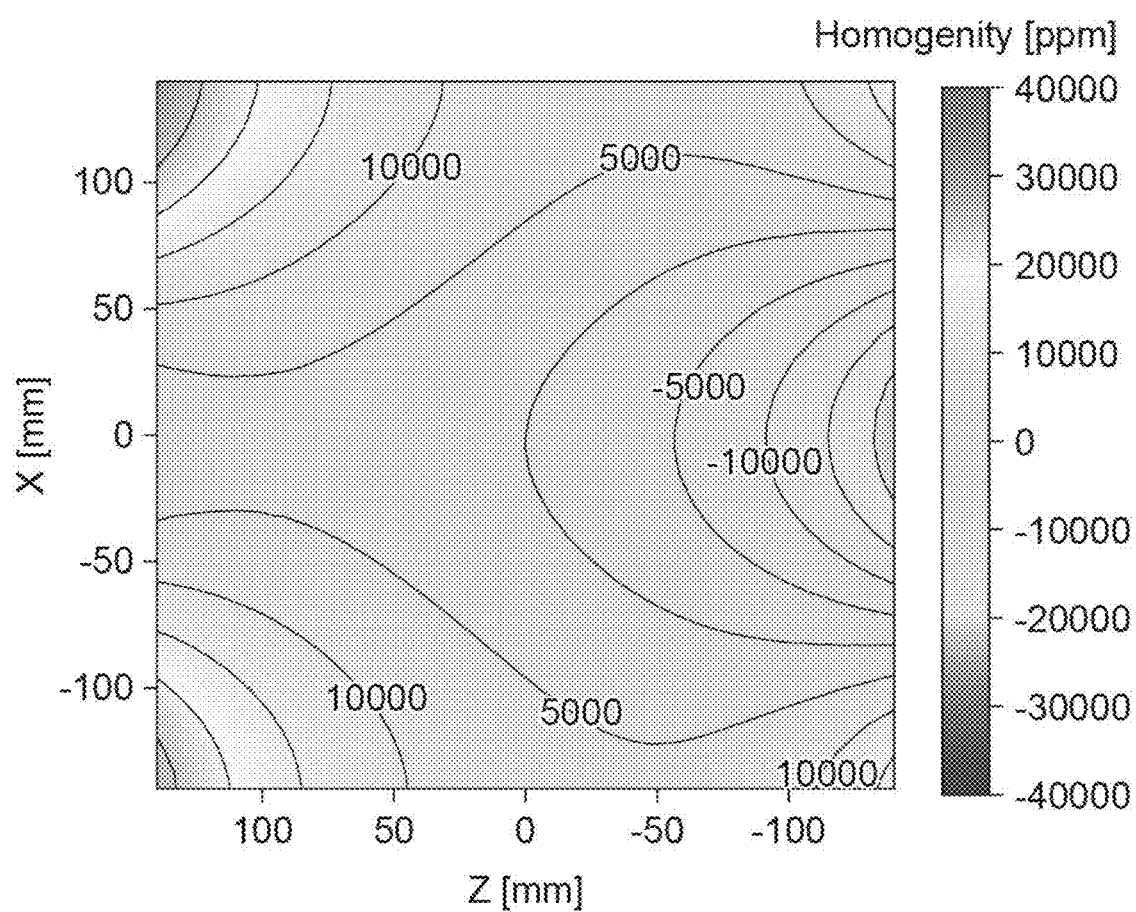
FIG. 11 is a graph showing a magnetic flux density distribution due to a magnetic field formed by the static magnetic field forming unit shown in FIG. 9.

FIGS. 10 and 11 are graphs showing the magnetic flux density distribution due to the magnetic field formed by the static magnetic field forming unit shown in FIG. 9. As shown in FIGS. 10 and 11, according to the static magnetic field forming unit 50A, when the diameter ϕb of the first holding member 54 is 75 mm, it is understood that an approximately uniform magnetic flux density distribution of 7.3 mT can be obtained in the range of at least about ϕ200 mm in the XZ plane. As described above, according to the static magnetic field forming unit 50A, the magnetic path from the first coil 53 to each of the first magnetic pole 51 and the second magnetic pole 52 can be made shorter, so that it is possible to obtain the uniform magnetic flux density distribution while improving the magnetic field strength (magnetic flux density) of the static magnetic field.

Figure 12:
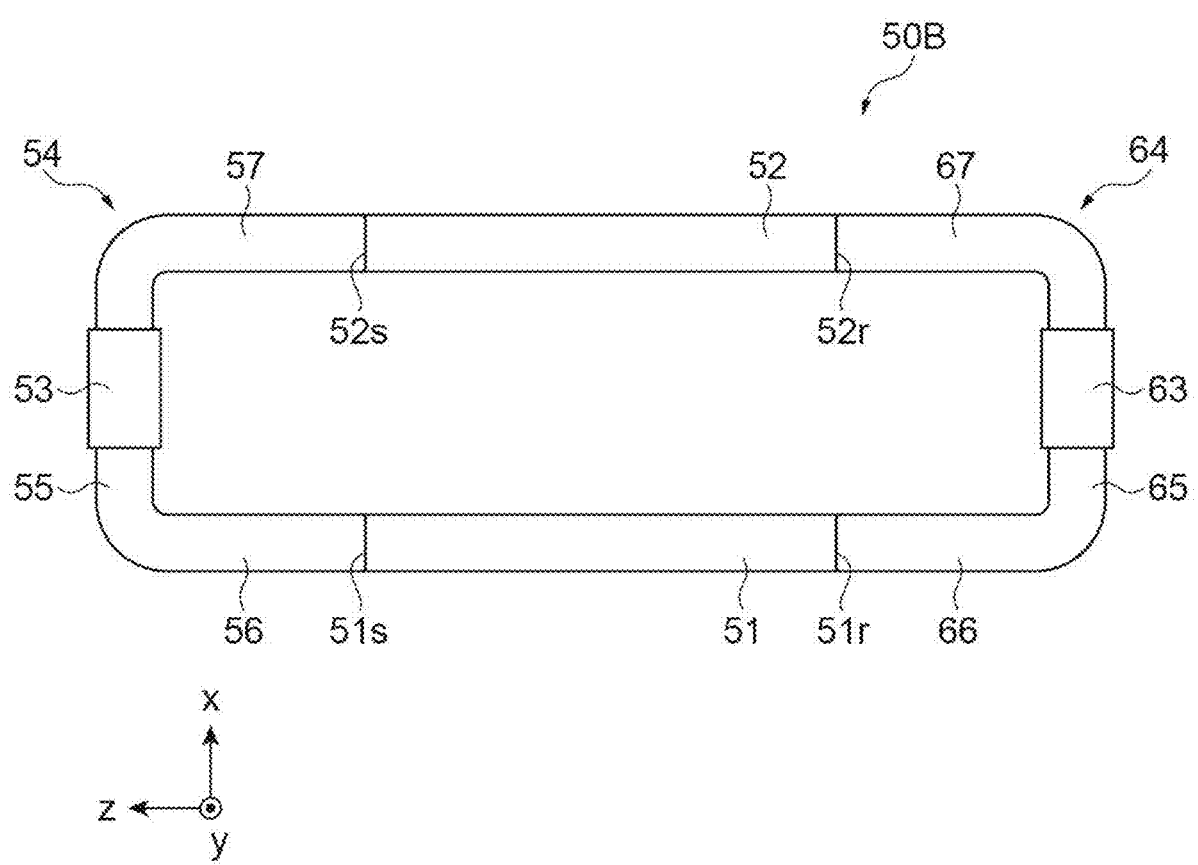
FIG. 12 is a side view showing a static magnetic field forming unit according to another modification example.

FIG. 12 is a side view showing a static magnetic field forming unit according to another modification example. A static magnetic field forming unit 50B shown in FIG. 12 is different from the static magnetic field forming unit 50A shown in FIG. 9 in that a second coil 63 for generating a magnetic flux and a second holding member 64, in which a magnetic path for guiding the magnetic flux generated by the second coil 63 to each of the first magnetic pole 51 and the second magnetic pole 52 is formed, are further provided.

The second holding member 64 includes a second main body portion 65 extending along the X-axis direction (first direction), a third extending portion 66 extending linearly from one end of the second main body portion 65 along the Z-axis direction, and a fourth extending portion 67 extending linearly from the other end of the second main body portion 65 along the Z-axis direction. The material of the second holding member 64, the shape and dimension of each portion, and the like may be the same as those of the first holding member 54.

In the static magnetic field forming unit 50B, the distal end of the third extending portion 66 is connected to an outer edge 51r of the first magnetic pole 51 on the third extending portion 66 side, and the distal end of the fourth extending portion 67 is connected to an outer edge 52r of the second magnetic pole 52 on the fourth extending portion 67 side. In addition, the second coil 63 is provided so as to be wound around the second main body portion 65, and the same one as the first coil 53 can be used as the second coil 63.

Figure 13:
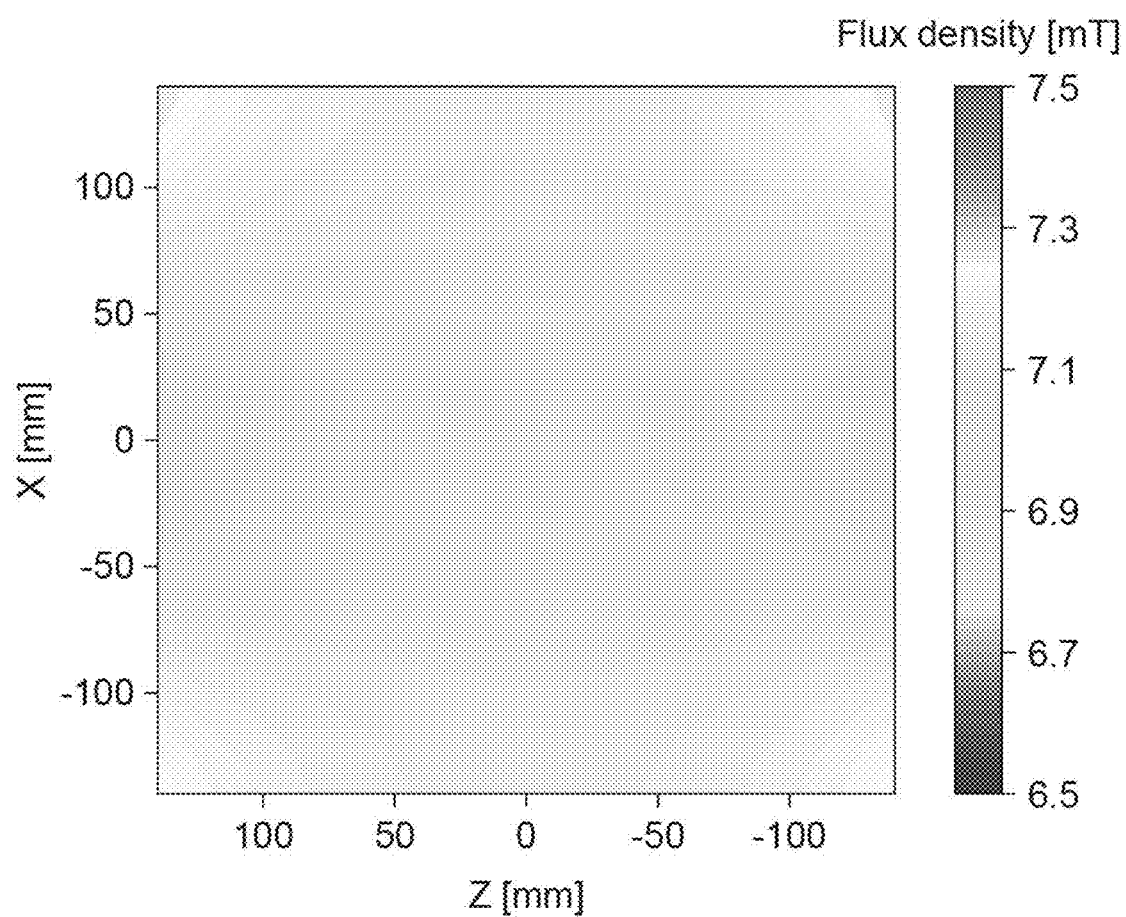
FIG. 13 is a graph showing a magnetic flux density distribution due to a magnetic field formed by the static magnetic field forming unit shown in FIG. 12.
Figure 14:
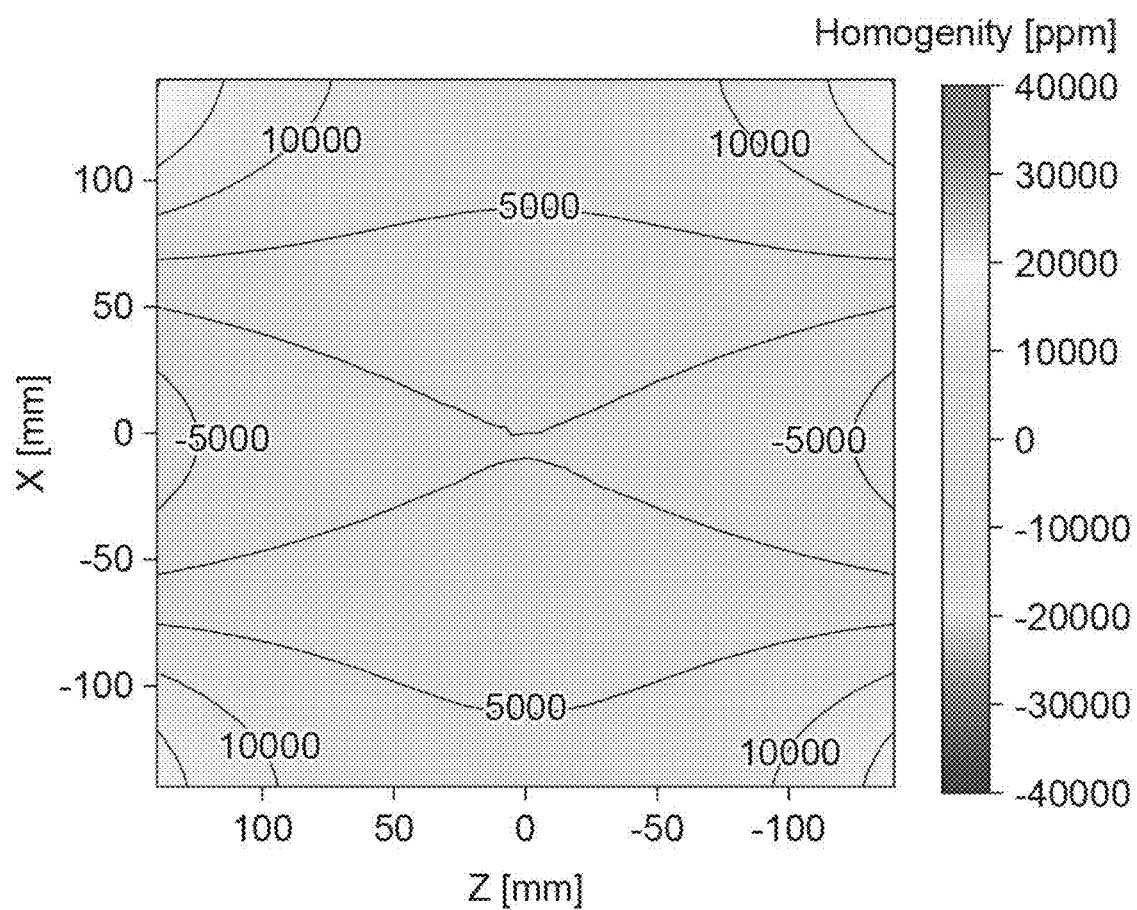
FIG. 14 is a graph showing a magnetic flux density distribution due to a magnetic field formed by the static magnetic field forming unit shown in FIG. 12.

FIGS. 13 and 14 are graphs showing the magnetic flux density distribution due to the magnetic field formed by the static magnetic field forming unit shown in FIG. 12. As shown in FIGS. 13 and 14, according to the static magnetic field forming unit 50B, when the diameter ϕb of each of the first holding member 54 and the second holding member 64 is 75 mm, it is understood that a more uniform magnetic flux density distribution of 7.1 mT can be obtained in the range of at least about ϕ200 mm in the XZ plane. As described above, according to the static magnetic field forming unit 50B, coils (the first coil 53 and the second coil 63) are arranged on both sides of the first magnetic pole 51 and the second magnetic pole 52, and the magnetic flux is guided from each of the coils to the first magnetic pole 51 and the second magnetic pole 52. Therefore, the uniformity of the static magnetic field formed in the measurement area AR is further improved.

Although the modification examples have been described above, any other modification examples are possible. For example, the multiple first coils 53 (or the multiple second coils 63) may be arranged in the first main body portion 55 (or the second main body portion 65). In this case as well, since the multiple first coils 53 (or the multiple second coils 63) are arranged so as to be symmetrical with respect to the reference line along the Z-axis direction, which is a line passing through the midpoint between the first magnetic pole 51 and the second magnetic pole 52 in the X-axis direction, it is possible to ensure the uniformity of the static magnetic field formed in the measurement area AR.

In addition, the shape and dimension of each portion of the static magnetic field forming units 50, 50A, and 50B, such as the first holding member 54 and the second holding member 64 or the first magnetic pole 51 and the second magnetic pole 52, can be arbitrarily adjusted.

The above embodiment will be noted below. In brain measurement apparatuses and brain measurement methods described in the following notes, each element can be arbitrarily replaced with and applied to each element of the above embodiment.

[Note 1] A brain measurement apparatus, including:
   a magnetoencephalograph including multiple optically pumped magnetometers configured to measure a brain's magnetic field, multiple magnetic sensors for geomagnetic field cancellation configured to measure a magnetic field relevant to geomagnetic field at a position of each of the multiple optically pumped magnetometers, multiple magnetic sensors for active shield configured to measure a fluctuating magnetic field at the position of each of the multiple optically pumped magnetometers, a geomagnetic field nulling coil for cancelling the magnetic field relevant to the geomagnetic field, and an active shield coil for cancelling the fluctuating magnetic field;
   an MRI apparatus including a static magnetic field coil for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse; and
   a controller configured to, when measuring the brain's magnetic field, control a current to be supplied to the geomagnetic field nulling coil and a current to be supplied to the active shield coil based on measured values of the multiple magnetic sensors for geomagnetic field cancellation and measured values of the multiple magnetic sensors for active shield and, when measuring an MR image, control the static magnetic field and the gradient magnetic field by controlling currents to be supplied to the static magnetic field coil and the gradient magnetic field coil and generate an MR image based on an output of the receive coil.

[Note 2] The brain measurement apparatus described in Note 1,
  in which the geomagnetic field nulling coil is formed by a geomagnetic field nulling coil for cancelling a magnetic field of the geomagnetic field and a gradient magnetic field nulling coil for cancelling a gradient magnetic field of the geomagnetic field.

[Note 3] The brain measurement apparatus described in Note 1 or 2,
  in which the controller determines a current to be supplied to the geomagnetic field nulling coil so as to generate a magnetic field for canceling the magnetic field relevant to the geomagnetic field, and determines a current to be supplied to the active shield coil so as to generate a magnetic field for canceling the fluctuating magnetic field.

[Note 4] The brain measurement apparatus described in any one of Notes 1 to 3,
  in which each of the geomagnetic field nulling coil and the active shield coil is a pair of coils arranged with the multiple optically pumped magnetometers interposed therebetween.

[Note 5] The brain measurement apparatus described in any one of Notes 1 to 4, further including:
  an output coil that is electrically connected to the receive coil and is configured to output a magnetic signal based on a current flowing through the receive coil; and
  another optically pumped magnetometer configured to detect the magnetic signal output by the output coil,
  in which the controller generates the MR image based on the magnetic signal detected by the another optically pumped magnetometer.

[Note 6] The brain measurement apparatus described in any one of Notes 1 to 5,
  in which the multiple optically pumped magnetometers are axial gradiometers having a measurement region and a reference region in a direction perpendicular to the scalp of a subject and coaxially.

[Note 7] The brain measurement apparatus described in any one of Notes 1 to 6,
  in which the multiple optically pumped magnetometers, the multiple magnetic sensors for geomagnetic field cancellation, the multiple magnetic sensors for active shield, and the receive coil are fixed to a helmet-type non-magnetic frame attached to the head of a subject.

[Note 8] The brain measurement apparatus described in any one of Notes 1 to 7, further including:
  an electromagnetic shield for shielding high-frequency electromagnetic noise.

[Note 9] The brain measurement apparatus described in Note 5,
  in which the multiple optically pumped magnetometers are configured to be applied a bias magnetic field so as to be sensitive to frequencies included in a range of 0 to 200 Hz, and
  the another optically pumped magnetometer is configured to be applied a bias magnetic field so as to be sensitive to frequencies included in a range of 20 kHz to 500 kHz.

[Note 10] A brain measurement method using a magnetoencephalograph including multiple optically pumped magnetometers configured to measure a brain's magnetic field, multiple magnetic sensors for geomagnetic field cancellation configured to measure a magnetic field relevant to geomagnetic field at a position of each of the multiple optically pumped magnetometers, multiple magnetic sensors for active shield configured to measure a fluctuating magnetic field at the position of each of the multiple optically pumped magnetometers, a geomagnetic field nulling coil for cancelling the magnetic field relevant to the geomagnetic field, and an active shield coil for cancelling the fluctuating magnetic field and an MRI apparatus including a static magnetic field coil for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse, the method including:
  when measuring the brain's magnetic field, controlling a current to be supplied to the geomagnetic field nulling coil and a current to be supplied to the active shield coil based on measured values of the multiple magnetic sensors for geomagnetic field cancellation and measured values of the multiple magnetic sensors for active shield; and
  when measuring an MR image, controlling the static magnetic field and the gradient magnetic field by controlling currents to be supplied to the static magnetic field coil and the gradient magnetic field coil and generating an MR image based on an output of the receive coil.

[Note 11] The brain measurement method described in Note 10,
  in which the geomagnetic field nulling coil is formed by a geomagnetic field nulling coil for cancelling a magnetic field of the geomagnetic field and a gradient magnetic field nulling coil for cancelling a gradient magnetic field of the geomagnetic field.

What is claimed is:

1. A brain measurement apparatus, comprising:
  a static magnetic field forming unit configured to form a static magnetic field in a measurement area;
  a gradient magnetic field coil configured to form a gradient magnetic field in the measurement area;
  a transmission coil configured to transmit a transmission pulse toward a subject in the measurement area;
  a detection coil configured to detect a nuclear magnetic resonance signal generated in the subject by transmission of the transmission pulse;
  a generator configured to generate an MR image based on the nuclear magnetic resonance signal detected by the detection coil; and
  an optically pumped magnetometer configured to measure a brain's magnetic field of the subject,
  wherein the static magnetic field forming unit includes:
  a first magnetic pole and a second magnetic pole arranged so as to face each other with the measurement area interposed therebetween;
  a first coil configured to generate a magnetic flux; and
  a first holding member which holds the first magnetic pole and the second magnetic pole and in which a magnetic path for guiding the magnetic flux generated by the first coil to each of the first magnetic pole and the second magnetic pole is formed.

2. The brain measurement apparatus according to claim 1, wherein the first holding member includes:
a first main body portion that extends along a first direction in which the first magnetic pole and the second magnetic pole face each other;
a first extending portion that extends from one end of the first main body portion along a second direction crossing the first direction; and
a second extending portion that extends from the other end of the first main body portion along the second direction,
the first magnetic pole is connected to and held by the first extending portion,
the second magnetic pole is connected to and held by the second extending portion, and
the first coil is provided so as to be wound around the first main body portion.

3. The brain measurement apparatus according to claim 2, wherein the first coil is provided in the first main body portion so as to be symmetrical with respect to a reference line along the second direction, which is a line passing through a midpoint between the first magnetic pole and the second magnetic pole in the first direction.

4. The brain measurement apparatus according to claim 2, wherein the first extending portion includes a first bent portion that is bent toward the second magnetic pole at an end portion of the first extending portion opposite to the first main body portion,
the second extending portion includes a second bent portion that is bent toward the first magnetic pole at an end portion of the second extending portion opposite to the first main body portion,
the first magnetic pole has a circular shape when viewed from the first direction and is connected to and held at a distal end of the first bent portion at a center of the circular shape, and
the second magnetic pole has a circular shape when viewed from the first direction and is connected to and held at a distal end of the second bent portion at a center of the circular shape.

5. The brain measurement apparatus according to claim 2, wherein the first extending portion and the second extending portion extend linearly along the second direction,
the first magnetic pole is connected to and held at a distal end of the first extending portion at an outer edge of the first magnetic pole on a side of the first extending portion, and
the second magnetic pole is connected to and held at a distal end of the second extending portion at an outer edge of the second magnetic pole on a side of the second extending portion.

6. The brain measurement apparatus according to claim 2, wherein the static magnetic field forming unit includes:
a second coil configured to generate a magnetic flux; and
a second holding member in which a magnetic path for guiding the magnetic flux generated by the second coil to each of the first magnetic pole and the second magnetic pole is formed,
the second holding member includes:
a second main body portion that extends along the first direction;
a third extending portion that extends linearly from one end of the second main body portion along the second direction; and
a fourth extending portion that extends linearly from the other end of the second main body portion along the second direction,
a distal end of the third extending portion is connected to an outer edge of the first magnetic pole on a side of the third extending portion,
a distal end of the fourth extending portion is connected to an outer edge of the second magnetic pole on a side of the fourth extending portion, and
the second coil is provided so as to be wound around the second main body portion.

7. The brain measurement apparatus according to claim 1, wherein a size of the first magnetic pole and a size of the second magnetic pole when viewed from a direction in which the first magnetic pole and the second magnetic pole face each other are larger than a distance between the first magnetic pole and the second magnetic pole.

8. A brain measurement apparatus, comprising:
a static magnetic field forming unit configured to form a static magnetic field in a measurement area;
a gradient magnetic field coil configured to form a gradient magnetic field in the measurement area;
a transmission coil configured to transmit a transmission pulse toward a subject in the measurement area;
a detection coil configured to detect a nuclear magnetic resonance signal generated in the subject by transmission of the transmission pulse; and
a generator configured to generate an MR image based on the nuclear magnetic resonance signal detected by the detection coil,
wherein the static magnetic field forming unit includes:
a first magnetic pole and a second magnetic pole arranged so as to face each other with the measurement area interposed therebetween;
a first coil configured to generate a magnetic flux;
a first holding member which holds the first magnetic pole and the second magnetic pole and in which a magnetic path for guiding the magnetic flux generated by the first coil to each of the first magnetic pole and the second magnetic pole is formed;
a second coil configured to generate a magnetic flux; and
a second holding member in which a magnetic path for guiding the magnetic flux generated by the second coil to each of the first magnetic pole and the second magnetic pole is formed,
the second holding member includes:
a second main body portion that extends along the first direction;
a third extending portion that extends linearly from one end of the second main body portion along the second direction; and
a fourth extending portion that extends linearly from the other end of the second main body portion along the second direction,
a distal end of the third extending portion is connected to an outer edge of the first magnetic pole on a side of the third extending portion,
a distal end of the fourth extending portion is connected to an outer edge of the second magnetic pole on a side of the fourth extending portion, and
the second coil is provided so as to be wound around the second main body portion.

* * * * *